(12) United States Patent
Nettekoven et al.

(10) Patent No.: US 8,673,950 B2
(45) Date of Patent: Mar. 18, 2014

(54) DIHYDROOXAZOL-2-AMINE DERIVATIVES

(75) Inventors: Matthias Nettekoven, Grenzach-Wyhlen (DE); Roger Norcross, Olsberg (CH); Alessandra Polara, Basel (CH)

(73) Assignee: Hoffmann-LaRoche Inc., Nutley, NJ (US)

( * ) Notice: Subject to any disclaimer, the term of this patent is extended or adjusted under 35 U.S.C. 154(b) by 135 days.

(21) Appl. No.: 13/279,362

(22) Filed: Oct. 24, 2011

(65) Prior Publication Data

US 2012/0108609 A1 May 3, 2012

(30) Foreign Application Priority Data

Nov. 2, 2010 (EP) .................................... 10189624

(51) Int. Cl.
*A61K 31/421* (2006.01)
*C07D 263/28* (2006.01)

(52) U.S. Cl.
USPC ........................................ 514/377; 548/233

(58) Field of Classification Search
USPC ......................................... 548/233; 514/377
See application file for complete search history.

(56) References Cited

U.S. PATENT DOCUMENTS

| 4,311,840 A | 1/1982 | Condon | |
|---|---|---|---|
| 8,354,441 B2 * | 1/2013 | Galley et al. .................. | 514/377 |

FOREIGN PATENT DOCUMENTS

| DE | 2253555 | 5/1974 |
|---|---|---|
| EP | 167459 A2 | 1/1986 |
| EP | 717037 | 6/1996 |
| WO | 02/076950 | 10/2002 |
| WO | 2008/092785 | 8/2008 |

OTHER PUBLICATIONS

Parker, E.M. et al., J. Pharmacol. Exp. Ther. 245:199-210 ( 1988).
Ueda et al., Bioorganic & Medicinal Chemistry Letters 14:313-316 ( 2004).
Mousseau, D.D. et al., Prog. Brain Res. 106:285-291 ( 1995).
Tuite, P. et al., Expert Opin. Investig. Drugs 12:1335-1352 ( 2003).
Usdin, E. et al., Psychopharmacology Series, Trace Amines and the Brain (Proceedings of a Study Group at the 14th Annual Meeting of the American College Of Neuropsychopharmacology, San Juan, Puerto Rico.), 1 ( 1976).
Deutch, A.Y. et al. Fundamental Neuroscience "Neurotransmitters" 2nd edition,Academic Press,:193-234 ( 1999).
Carlsson, A. et al., Annu. Rev. Pharmacol. Toxicol. 41:237-260 ( 2001).
Premont, R. T. et al., Proc. Natl. Acad. Sci. USA 98:9474-9475 ( 2001).
(International Search Report for PCT/EP2011/068705 Feb. 2, 2012).
Agami et al., Tetrahedron 57:195-200 ( 2001).
McCormack, J.K. et al., J. Neurosci. 6:94-101 ( 1986).
Lindemann, L. et al., Genomics 85:372-385 ( 2005).
Lindemann, L. et al., Trends in Pharmacol. Sci, 26:274-281 ( 2005).
Castellanos, F.X. et al., Nat. Rev. Neurosci. 3:617-628 ( 2002).
Dyck, L.E., Life Sci. 44:1149-1156 ( 1989).
Branchek, T. A. et al., Curr. Opin. Pharmacol. 3:90-97 ( 2003).
Wong, M.L. et al., Nat. Rev. Neurosci. 2:343-351 ( 2001).

* cited by examiner

*Primary Examiner* — Patricia L Morris

(57) ABSTRACT

The invention relates to compounds of formula

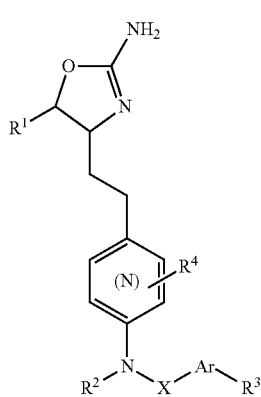

wherein $R^1$, $R^2$, $R^3$, $R^4$, X, Ar, and

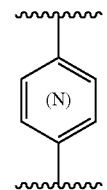

are defined herein
or to a pharmaceutically suitable acid addition salt thereof.
Compounds of formula I have a good affinity to the trace amine associated receptors (TAARs), especially for TAAR1. The compounds can be used for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm and cardiovascular disorders.

10 Claims, No Drawings

DIHYDROOXAZOL-2-AMINE DERIVATIVES

PRIORITY TO RELATED APPLICATION(S)

This application claims the benefit of European Patent Application No. 10189624.9, filed Nov. 2, 2010, which is hereby incorporated by reference in its entirety.

BACKGROUND OF THE INVENTION

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlaps with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gas. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

Therefore, there is a broad interest to increase the knowledge about trace amine associated receptors.

References Used:
1 Deutch, A. Y. and Roth, R. H. (1999) Neurotransmitters. In *Fundamental Neuroscience* (2$^{nd}$ edn) (Zigmond, M. J., Bloom, F. E., Landis, S. C., Roberts, J. L, and Squire, L. R., eds.), pp. 193-234, Academic Press;
2 Wong, M. L. and Licinio, J. (2001) Research and treatment approaches to depression. *Nat. Rev. Neurosci.* 2, 343-351;
3 Carlsson, A. et al. (2001) Interactions between monoamines, glutamate, and GABA in schizophrenia: new evidence. *Annu. Rev. Pharmacol. Toxicol.* 41, 237-260;
4 Tuite, P. and Riss, J. (2003) Recent developments in the pharmacological treatment of Parkinson's disease. *Expert Opin. Investig. Drugs* 12, 1335-1352,
5 Castellanos, F. X. and Tannock, R. (2002) Neuroscience of attention-deficit/hyperactivity disorder: the search for endophenotypes. *Nat. Rev. Neurosci.* 3, 617-628;
6 Usdin, Earl; Sandler, Merton; Editors. *Psychopharmacology Series, Vol.* 1: *Trace Amines and the Brain. [Proceedings of a Study Group at the* 14*th Annual Meeting of the American College of Neuropsychoparmacology*, San Juan, Puerto Rico] (1976);
7 Lindemann, L. and Hoener, M. (2005) A renaissance in trace amines inspired by a novel GPCR family. *Trends in Pharmacol. Sci.* 26, 274-281;
8 Branchek, T. A. and Blackburn, T. P. (2003) Trace amine receptors as targets for novel therapeutics: legend, myth and fact. *Curr. Opin. Pharmacol.* 3, 90-97;
9 Premont, R. T. et al. (2001) Following the trace of elusive amines. *Proc. Natl. Acad. Sci. U.S.A.* 98, 9474-9475;
10 Mousseau, D. D. and Butterworth, R. F. (1995) A high-affinity [3H] tryptamine binding site in human brain. *Prog. Brain Res.* 106, 285-291;
11 McCormack, J. K. et al. (1986) Autoradiographic localization of tryptamine binding sites in the rat and dog central nervous system. *J. Neurosci.* 6, 94-101;
12 Dyck, L. E. (1989) Release of some endogenous trace amines from rat striatal slices in the presence and absence of a monoamine oxidase inhibitor. *Life Sci.* 44, 1149-1156;
13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;
14 Lindemann, L. et al. (2005) Trace amine associated receptors form structurally and functionally distinct subfamilies of novel G protein-coupled receptors. *Genomics* 85, 372-385.

SUMMARY OF THE INVENTION

The invention provides compounds of formula

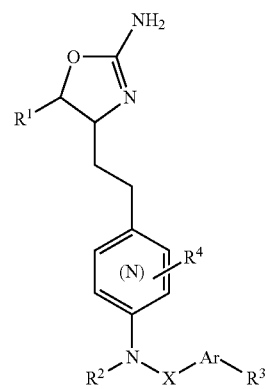

wherein
$R^1$ is hydrogen or lower alkyl;
$R^2$ is hydrogen or is heteroaryl, optionally substituted by one or more halogen, lower alkyl, lower alkyl substituted by halogen, lower alkoxy, lower alkoxy substituted by halogen, cyano, S-lower alkyl, S(O)-lower alkyl, S(O)$_2$-lower alkyl, C(O)-lower alkyl or C$_{3-6}$-cycloalkyl;

R$^3$ is hydrogen, halogen, lower alkyl, lower alkyl substituted by halogen, lower alkoxy, lower alkoxy substituted by halogen, cyano, S-lower alkyl, S(O)-lower alkyl, S(O)$_2$-lower alkyl, C(O)-lower alkyl or C$_{3-6}$-cycloalkyl;

R$^4$ is hydrogen or lower alkyl;

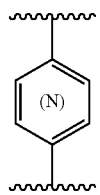

is phenyl or pyridinyl, wherein the N-atom may be in different positions;

X is a bond or —CH(CF$_3$)—;

Ar is aryl or heteroaryl, optionally substituted by one or more R$^3$;

or a pharmaceutically suitable acid addition salt thereof.

The invention includes all racemic mixtures, all their corresponding enantiomers and/or optical isomers. In addition, all tautomeric forms of compounds of formula I are also encompassed by the present invention.

Compounds of formula I have a good affinity to the trace amine associated receptors (TAARs), especially for TAAR1.

The compounds can be used for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain medicaments having selectivity for the TAAR1 receptor vs. adrenergic receptors. Compounds of the present invention show selectivity for TAAR1 receptor over adrenergic receptors, in particular good selectivity vs. the human and rat alpha1 and alpha2 adrenergic receptors.

The present invention provides new compounds of formula I and their pharmaceutically acceptable salts, pharmaceutical compositions containing them, and methods for the manufacture of the compounds and compositions. The present invention further provides methods for the treatment of diseases related to the biological function of the trace amine associated receptors, their manufacture and medicaments based on a compound in accordance with the invention in the control or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, diabetes, anxiety and attention deficit hyperactivity disorder (ADHD).

DETAILED DESCRIPTION OF THE INVENTION

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group wherein an alkyl residue as defined above is attached via an oxygen atom.

As used herein, the term "lower alkyl substituted by halogen" denotes an alkyl group as defined above, wherein at least one hydrogen atom is replaced by halogen, for example CF$_3$, CHF$_2$, CH$_2$F, CH$_2$CF$_3$, CH$_2$CH$_2$CF$_3$, CH$_2$CF$_2$CF$_3$ and the like.

As used herein, the term "lower alkoxy substituted by halogen" denotes a group wherein the alkyl residue is as defined above and which is attached via an oxygen atom and wherein at least on hydrogen atom is replaced by halogen.

The term "halogen" denotes chlorine, iodine, fluorine and bromine.

The term "cycloalkyl" is an alkylene ring containing from 3 to 6 carbon ring atoms.

The term "aryl" denotes an aromatic carbon ring such as phenyl or naphthyl, preferably the phenyl.

The term "heteroaryl" refers to an aromatic 6 membered monocyclic ring or to a 10 membered bicyclic ring which contains 1, 2 or 3 heteroatoms selected from nitrogen, such as pyridinyl, pyridazinyl, pyrimidinyl, pyrazinyl or quinolinyl. Preferred heteroaryl groups are pyridinyl, pyrimidinyl, pyrazinyl or quinolinyl.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgment of the attending medical or veterinary practitioner, and other factors.

One embodiment of the invention provides compounds of formula Ia,

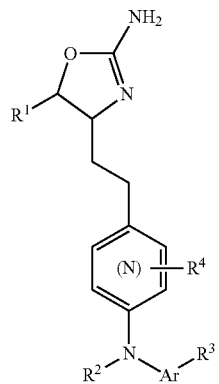

R¹ is hydrogen or lower alkyl;
R² is hydrogen or is heteroaryl, optionally substituted by one or more halogen, lower alkyl, lower alkyl substituted by halogen, lower alkoxy, lower alkoxy substituted by halogen, cyano, S-lower alkyl, S(O)-lower alkyl, S(O)₂-lower alkyl, C(O)-lower alkyl or $C_{3-6}$-cycloalkyl;
R³ is hydrogen, halogen, lower alkyl, lower alkyl substituted by halogen, lower alkoxy, lower alkoxy substituted by halogen, cyano, S-lower alkyl, S(O)-lower alkyl, S(O)₂-lower alkyl, C(O)-lower alkyl or $C_{3-6}$-cycloalkyl;
R⁴ is hydrogen or lower alkyl;

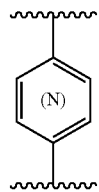

is phenyl or pyridinyl, wherein the N-atom may be in different positions;
Ar is aryl or heteroaryl, optionally substituted by one or more R³;
or a pharmaceutically suitable acid addition salt thereof.

A group of compounds of formula Ia are those, wherein Ar is aryl, selected from phenyl or naphthyl, for example the following compounds:
(S)-4-(4-(Naphthalen-1-ylamino)phenethyl)-4,5-dihydrooxazol-2-amine;
(S)-4-(4-(8-Chloronaphthalen-1-ylamino)phenethyl)-4,5-dihydrooxazol-2-amine;
(S)-4-{2-[4-(4-Chloro-phenylamino)-phenyl]-ethyl}-4,5-dihydro-oxazol-2-ylamine;
(S)-4-{2-[4-(4-Chloro-2-fluoro-phenylamino)-phenyl]-ethyl}-4,5-dihydro-oxazol-2-ylamine;
(S)-4-{2-[4-(4-Trifluoromethyl-phenylamino)-phenyl]-ethyl}-4,5-dihydro-oxazol-2-ylamine;
(S)-4-{2-[4-(4-Methoxy-phenylamino)-phenyl]-ethyl}-4,5-dihydro-oxazol-2-ylamine;
(S)-4-(4-(3-Methyl-4-(trifluoromethoxy)phenylamino)phenethyl)-4,5-dihydrooxazol-2-amine;
(S)-4-[2-(4-Phenylamino-phenyl)-ethyl]-4,5-dihydro-oxazol-2-ylamine;
(S)-4-(4-(p-Tolylamino)phenethyl)-4,5-dihydrooxazol-2-amine and
(S)-4-(4-(3,4-Dichlorophenylamino)phenethyl)-4,5-dihydrooxazol-2-amine.

A further group of compounds disclosed in formula Ia are those, wherein Ar is heteroaryl, selected from pyridinyl, pyridazinyl, pyrimidinyl, pyrazinyl and quinolinyl, for example the following compounds
(S)-4-(4-(Quinolin-8-ylamino)phenethyl)-4,5-dihydrooxazol-2-amine;
(S)-4-(4-(5-Fluoropyridin-2-ylamino)phenethyl)-4,5-dihydrooxazol-2-amine;
(S)-4-(4-(6-Methylquinolin-8-ylamino)phenethyl)-4,5-dihydrooxazol-2-amine;
{4-[2-((S)-2-Amino-4,5-dihydro-oxazol-4-yl)-ethyl]-phenyl}-(5-trifluoromethyl-pyridin-2-yl)-amine;
{4-[2-((S)-2-Amino-4,5-dihydro-oxazol-4-yl)-ethyl]-phenyl}-(5-chloro-pyridin-2-yl)-amine;
6-{-4-[2-((S)-2-Amino-4,5-dihydro-oxazol-4-yl)-ethyl]-phenylamino}-nicotinonitrile;
(S)-4-(4-(6-(Trifluoromethyl)pyrimidin-4-ylamino)phenethyl)-4,5-dihydrooxazol-2-amine;
{4-[2-((S)-2-Amino-4,5-dihydro-oxazol-4-yl)-ethyl]-phenyl}-(5-chloro-pyrimidin-2-yl)-amine;
{4-[2-((S)-2-Amino-4,5-dihydro-oxazol-4-yl)-ethyl]-phenyl}-(5-fluoro-pyrimidin-2-yl)-amine;
{4-[2-((S)-2-Amino-4,5-dihydro-oxazol-4-yl)-ethyl]-phenyl}-(3-fluoro-pyridin-2-yl)-amine;
{4-[2-((S)-2-Amino-4,5-dihydro-oxazol-4-yl)-ethyl]-phenyl}-(4-fluoro-pyridin-2-yl)-amine;
{4-[2-((S)-2-Amino-4,5-dihydro-oxazol-4-yl)-ethyl]-phenyl}-(4-trifluoromethyl-pyridin-2-yl)-amine;
{4-[2-((S)-2-Amino-4,5-dihydro-oxazol-4-yl)-ethyl]-phenyl}-(6-methyl-pyrimidin-4-yl)-amine;
{4-[2-((S)-2-Amino-4,5-dihydro-oxazol-4-yl)-ethyl]-phenyl}-(6-methyl-pyridin-2-yl)-amine;
{4-[2-((S)-2-Amino-4,5-dihydro-oxazol-4-yl)-ethyl]-phenyl}-(6-trifluoromethyl-pyridin-2-yl)-amine;
{4-[2-((S)-2-Amino-4,5-dihydro-oxazol-4-yl)-ethyl]-phenyl}-(6-chloro-pyrazin-2-yl)-amine;
{4-[2-((S)-2-Amino-4,5-dihydro-oxazol-4-yl)-ethyl]-phenyl}-(6-chloro-pyridin-2-yl)-amine;
{4-[2-((S)-2-Amino-4,5-dihydro-oxazol-4-yl)-ethyl]-phenyl}-(5-methyl-pyridin-2-yl)-amine;
{4-[2-((S)-2-Amino-4,5-dihydro-oxazol-4-yl)-ethyl]-phenyl}-(5-methoxy-pyridin-2-yl)-amine;
6-{-4-[2-((S)-2-Amino-4,5-dihydro-oxazol-4-yl)-ethyl]-phenylamino}-pyrazine-2-carbonitrile;
{4-[2-((S)-2-Amino-4,5-dihydro-oxazol-4-yl)-ethyl]-phenyl}-(6-chloro-pyrimidin-4-yl)-amine;
{4-[2-((S)-2-Amino-4,5-dihydro-oxazol-4-yl)-ethyl]-phenyl}-(6-methoxy-pyrimidin-4-yl)-amine;
{4-[2-((S)-2-Amino-4,5-dihydro-oxazol-4-yl)-ethyl]-phenyl}-(2-methyl-pyrimidin-4-yl)-amine;
(S)-4-(4-(Pyrimidin-4-ylamino)phenethyl)-4,5-dihydrooxazol-2-amine hydrochloride;
{4-[2-((S)-2-Amino-4,5-dihydro-oxazol-4-yl)-ethyl]-phenyl}-(4-methoxy-pyrimidin-2-yl)-amine;
{4-[2-((S)-2-Amino-4,5-dihydro-oxazol-4-yl)-ethyl]-phenyl}-(5-ethyl-pyrimidin-2-yl)-amine;
{4-[2-((S)-2-Amino-4,5-dihydro-oxazol-4-yl)-ethyl]-phenyl}-(5-methoxy-pyrimidin-2-yl)-amine;
5-{-4-[2-((S)-2-Amino-4,5-dihydro-oxazol-4-yl)-ethyl]-phenylamino}-pyrazine-2-carbonitrile;
{4-[2-((S)-2-Amino-4,5-dihydro-oxazol-4-yl)-ethyl]-phenyl}-(4-trifluoromethyl-pyrimidin-2-yl)-amine;

{4-[2-((S)-2-Amino-4,5-dihydro-oxazol-4-yl)-ethyl]-phenyl}-(3-chloro-pyrazin-2-yl)-amine;
{4-[2-((S)-2-Amino-4,5-dihydro-oxazol-4-yl)-ethyl]-phenyl}-(6-chloro-4-trifluoromethyl-pyridin-2-yl)-amine;
{4-[2-((S)-2-Amino-4,5-dihydro-oxazol-4-yl)-ethyl]-phenyl}-(6-methyl-pyrazin-2-yl)-amine;
{4-[2-((S)-2-Amino-4,5-dihydro-oxazol-4-yl)-ethyl]-phenyl}-(6-chloro-2-methoxy-pyrimidin-4-yl)-amine;
{4-[2-((S)-2-Amino-4,5-dihydro-oxazol-4-yl)-ethyl]-phenyl}-(4-methylsulfanyl-pyrimidin-2-yl)-amine;
{4-[2-((S)-2-Amino-4,5-dihydro-oxazol-4-yl)-ethyl]-phenyl}-(5-methyl-pyrimidin-2-yl)-amine;
1-(2-{4-[2-((S)-2-Amino-4,5-dihydro-oxazol-4-yl)-ethyl]-phenylamino}-pyrimidin-5-yl)-ethanone;
{4-[2-((S)-2-Amino-4,5-dihydro-oxazol-4-yl)-ethyl]-phenyl}-(4-methyl-pyrimidin-2-yl)-amine;
{4-[2-((S)-2-Amino-4,5-dihydro-oxazol-4-yl)-ethyl]-phenyl}-(5-propyl-pyrimidin-2-yl)-amine;
{4-[2-((S)-2-Amino-4,5-dihydro-oxazol-4-yl)-ethyl]-phenyl}-(2-chloro-pyrimidin-5-yl)-amine;
{4-[2-((S)-2-Amino-4,5-dihydro-oxazol-4-yl)-ethyl]-phenyl}-(5-bromo-pyrimidin-2-yl)-amine;
{4-[2-((4S,5S)-2-Amino-5-methyl-4,5-dihydro-oxazol-4-yl)-ethyl]-phenyl}-(5-chloro-pyrimidin-2-yl)-amine;
{4-[2-((S)-2-Amino-4,5-dihydro-oxazol-4-yl)-ethyl]-phenyl}-(5-cyclopropyl-pyrimidin-2-yl)-amine;
{4-[2-((S)-2-Amino-4,5-dihydro-oxazol-4-yl)-ethyl]-phenyl}-(5-ethoxy-pyrimidin-2-yl)-amine;
(S)-4-(4-(5-(Trifluoromethyl)pyrimidin-2-ylamino)phenethyl)-4,5-dihydrooxazol-2-amine;
(S)-4-(4-(5-tert-Butylpyrimidin-2-ylamino)phenethyl)-4,5-dihydrooxazol-2-amine;
(S)-4-(4-(5-(Pentan-3-yl)pyrimidin-2-ylamino)phenethyl)-4,5-dihydrooxazol-2-amine;
2-{-4-[2-((S)-2-Amino-4,5-dihydro-oxazol-4-yl)-ethyl]-phenylamino}-pyrimidine-5-carbonitrile;
(S)-4-(4-(5-Cyclobutylpyrimidin-2-ylamino)phenethyl)-4,5-dihydrooxazol-2-amine;
(S)-4-(4-(5-Isopropylpyrimidin-2-ylamino)phenethyl)-4,5-dihydrooxazol-2-amine;
{4-[2-((S)-2-Amino-4,5-dihydro-oxazol-4-yl)-ethyl]-2-methyl-phenyl}-(5-chloro-pyrimidin-2-yl)-amine and
(S)-4-(4-(5-(2,2,2-Trifluoroethoxy)pyrimidin-2-ylamino)phenethyl)-4,5-dihydrooxazol-2-amine.

A further embodiment provides compounds of formula Ib

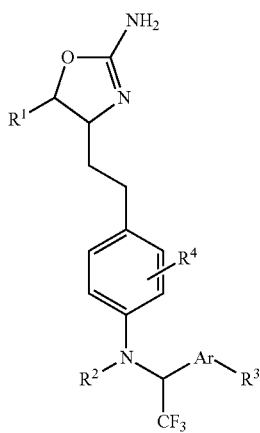

Ib $R^1$ is hydrogen or lower alkyl;
$R^2$ is hydrogen or is heteroaryl, optionally substituted by one or more halogen, lower alkyl, lower alkyl substituted by halogen, lower alkoxy, lower alkoxy substituted by halogen, cyano, S-lower alkyl, S(O)-lower alkyl, S(O)$_2$-lower alkyl, C(O)-lower alkyl or $C_{3-6}$-cycloalkyl;
$R^3$ is hydrogen, halogen, lower alkyl, lower alkyl substituted by halogen, lower alkoxy, lower alkoxy substituted by halogen, cyano, S-lower alkyl, S(O)-lower alkyl, S(O)$_2$-lower alkyl, C(O)-lower alkyl or $C_{3-6}$-cycloalkyl;
$R^4$ is hydrogen or lower alkyl;

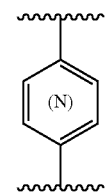

is phenyl or pyridinyl, wherein the N-atom may be in different positions;

Ar is aryl or heteroaryl, optionally substituted by one or more $R^3$;

or a pharmaceutically suitable acid addition salt thereof.

A group of compounds from of Ib are those, wherein Ar is aryl, selected from phenyl or naphthyl, for example the following compounds:

(4S)-4-(4-(1-(4-Chlorophenyl)-2,2,2-trifluoroethylamino)phenethyl)-4,5-dihydrooxazol-2-amine (1:1 mixture of epimers);
(+)-(S)-4-(4-((S)-1-(4-Chlorophenyl)-2,2,2-trifluoroethylamino)phenethyl)-4,5-dihydrooxazol-2-amine;
(−)-(S)-4-(4-((R)-1-(4-chlorophenyl)-2,2,2-trifluoroethylamino)phenethyl)-4,5-dihydrooxazol-2-amine;
(4S)-4-(4-(2,2,2-Trifluoro-1-(3-fluorophenyl)ethylamino)phenethyl)-4,5-dihydrooxazol-2-amine and
(4S)-4-(4-(2,2,2-Trifluoro-1-(4-(trifluoromethyl)phenyl)ethylamino)phenethyl)-4,5-dihydrooxazol-2-amine.

A group of compounds of formula Ib are those, wherein Ar is heteroaryl, selected from pyridinyl, pyridazinyl, pyrimidinyl, pyrazinyl and quinolinyl.

A further embodiment of the invention provides compounds of formula I, wherein

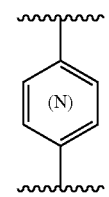

is pyridinyl, for example the compound
{5-[2-((S)-2-Amino-4,5-dihydro-oxazol-4-yl)-ethyl]-pyridin-2-yl}-(5-chloro-pyrimidin-2-yl)-amine.

The present compounds of formula I and their pharmaceutically acceptable salts can be prepared by methods known in the art, for example, by processes described below, which process comprises a) cyclising a compound of formula

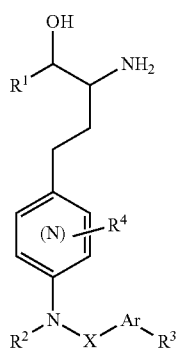

with cyanogen bromide (BrCN) to provide a compound of formula

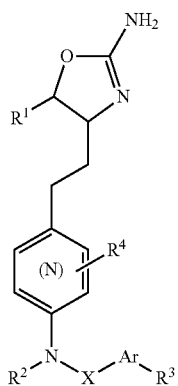

I wherein the definitions for $R^1$, $R^2$, $R^3$, $R^4$, Ar and X are as described above, and, if desired, converting the compounds obtained into pharmaceutically acceptable acid addition salts.

The preparation of compounds of formula I of the present invention can be carried out in sequential or convergent synthetic routes. Syntheses of the compounds of the invention are shown in the following schemes 1-5 and in the description for preparation of the specific compounds 1-75. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1 to 5, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

GENERAL PROCEDURE

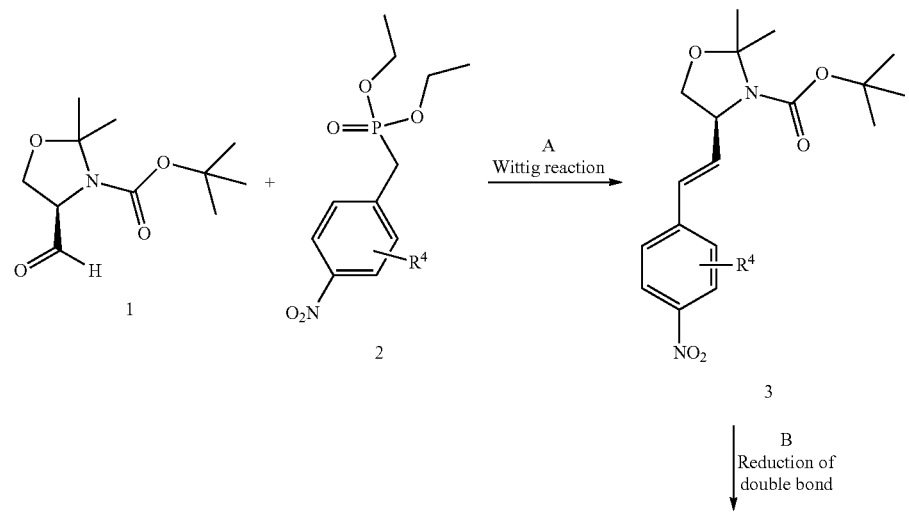

Scheme 1

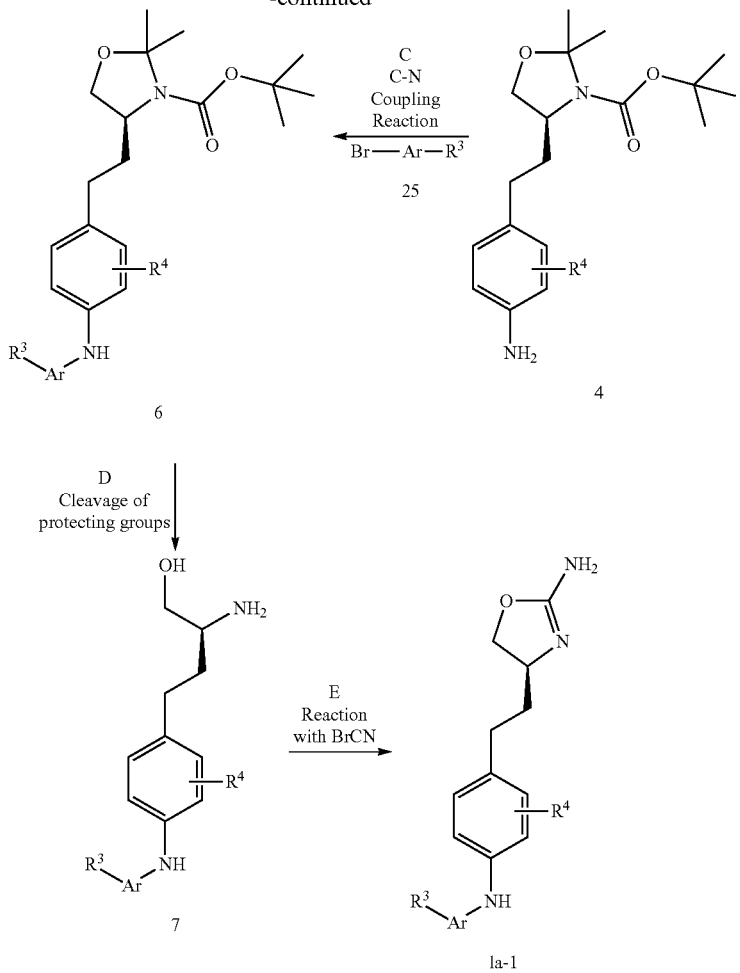

$R^3$, $R^4$, and Ar are as described above.

Step A: Wittig reaction between aldehyde 1 (CAS 95715-87-0) and phosphonate ester 2 (4-nitro-benzyl)-phosphonic acid diethyl ester [CAS 2609-49-6] or (3-methyl-4-nitro-benzyl)-phosphonic acid diethyl ester [CAS 873458-20-9]) can be accomplished by using a base such as NaH, KOtBu, NaOMe, NaOEt, n-BuLi, LiHMDS, NaHMDS, KHMDS, LDA in a solvent such as THF, dioxane, acetonitrile, 1,2-dimethoxyethane, DMF, benzene, toluene or mixtures thereof at temperatures from −78° C. to 80° C. for 15 min-8 hrs and if appropriate optional addition of a crown ether for ylide generation and then condensing the ylide with the carbonyl compound in the same solvent at a temperature between 0 and 80° C. for 1-24 hrs. Alternatively, the base, the carbonyl compound and the optional crown ether can be added to the reaction mixture at the same time without pre-formation of the ylide at temperatures from −78° C. to 80° C.

Preferred conditions are ylide formation at −78° C. using LDA (prepared in situ from treatment of N,N-diisopropylamine with n-BuLi) as base and THF as solvent, reacting the phosphonic acid ester for 1 hour at −78° C., and then condensation with the carbonyl component warming to room temperature overnight.

Step B: Reduction of the alkene 3 with concomitant reduction of the nitro group can be effected by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, $H_2O$, dioxane, THF, HOAc, EtOAc $CH_2Cl_2$, $CHCl_3$, DMF or mixtures thereof.

Preferred conditions are ammonium formate in the presence of palladium on charcoal in MeOH at 50° C. for 1 hour.

Step C: C—N bond formation can be accomplished by treatment of aryl amine 4 with aryl bromide 5 in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium chloroform complex, catalytic 9,9-dimethyl-4,5-bis(diphenylphosphino)xanthene (xantphos) and caesium carbonate in dioxane in a sealed tube heated at 110° C. overnight according to a modification of the procedure of van Leeuwen and co-workers (*Tetrahedron. Lett.* 1999, 40, 3789-3790).

Alternative preferred conditions are catalytic palladium(II) acetate, catalytic 2,2'-bis(diphenylphosphino)-1,1'-binaphthalene (BINAP) and potassium carbonate in toluene in a sealed tube heated at 110° C. for 1 hour according to the procedure of Dommisse and co-workers (*Tetrahedron* 2001, 57, 7027-7034).

Step D: Simultaneous cleavage of the amino alcohol protecting groups of 6 can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 80° C.

Preferred conditions are $CF_3COOH$ in aqueous acetonitrile at 80° C. for 2 hours or 4 N HCl in dioxane and THF at 60° C. for 2 hours.

Step E: Cyclisation of the amino alcohol 7 to the corresponding 2-aminooxazoline Ia-1 can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight followed by treatment with aqueous ammonia solution at room temperature for 1 hour.

Preferred conditions are methanol as solvent and sodium acetate as base at r.t. overnight followed by treatment with aqueous ammonia solution at room temperature for 1 hour.

Scheme 2

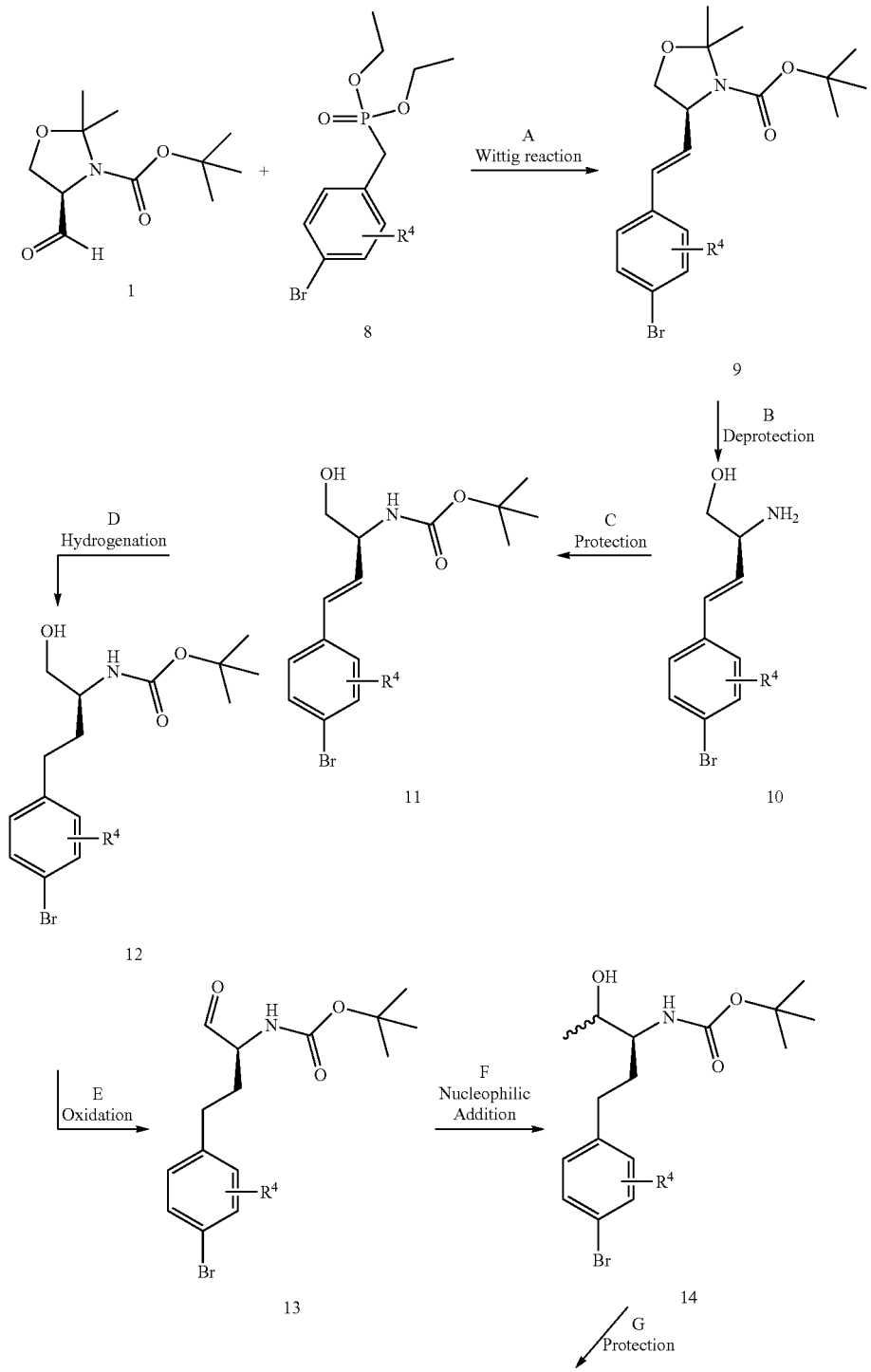

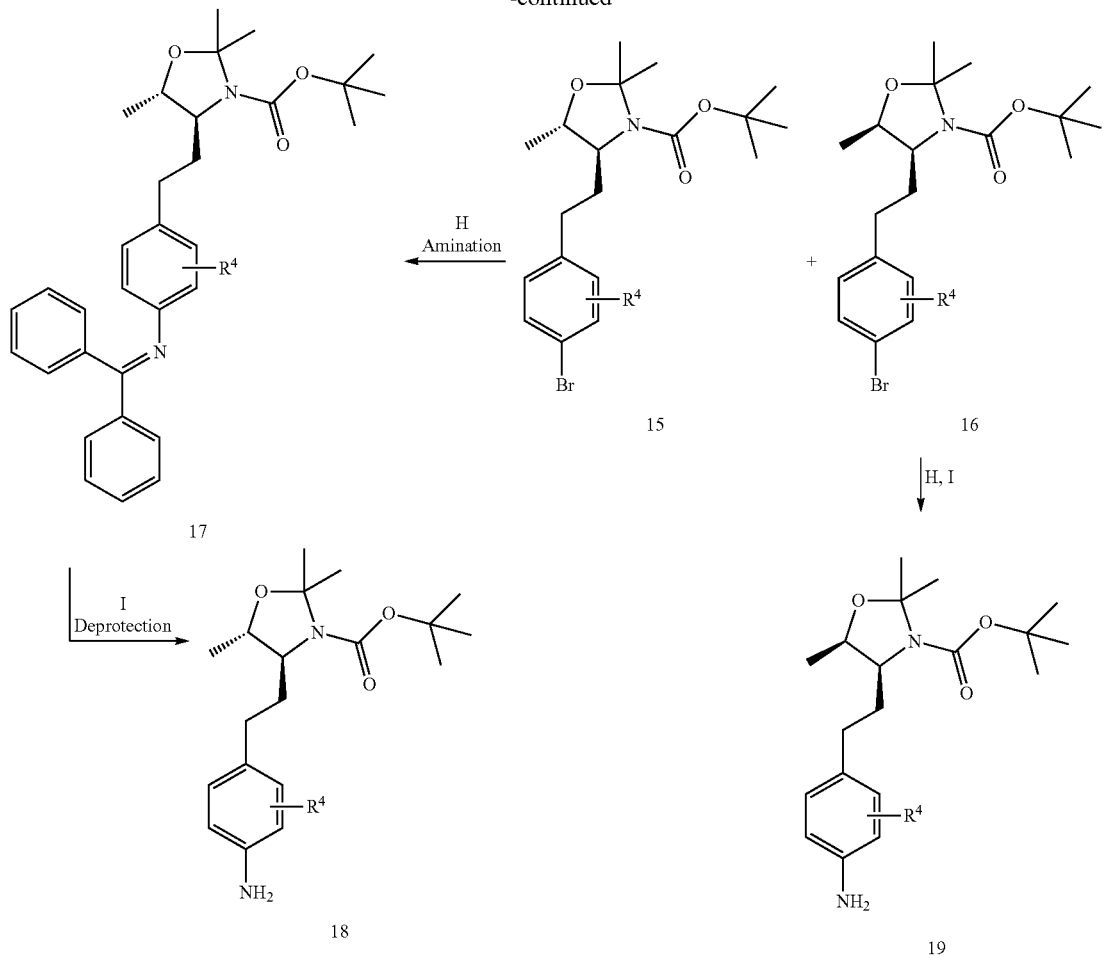

Step A: Wittig reaction between aldehyde 2 (CAS 95715-87-0) and (4-bromo-benzyl)-phosphonic acid diethyl ester 8 (CAS 38186-51-5) can be accomplished by using a base such as NaH, KOtBu, NaOMe, NaOEt, n-BuLi, LiHMDS, NaHMDS, KHMDS, LDA in a solvent such as THF, dioxane, acetonitrile, 1,2-dimethoxyethane, DMF, benzene, toluene or mixtures thereof at temperatures from −78° C. to 80° C. for 15 min-8 hrs and if appropriate optional addition of a crown ether for ylide generation and then condensing the ylide with the carbonyl compound in the same solvent at a temperature between 0 and 80° C. for 1-24 hrs. Alternatively, the base, the carbonyl compound and the optional crown ether can be added to the reaction mixture at the same time without pre-formation of the ylide at temperatures from −78° C. to 80° C.

Preferred conditions are ylide formation at −78° C. using LDA (prepared in situ from treatment of N,N-diisopropylamine with n-BuLi) as base and THF as solvent, reacting the phosphonic acid ester for 1 hour at −78° C., and then condensation with the carbonyl component warming to room temperature overnight.

Step B: Simultaneous cleavage of the protecting groups of 9 to afford amino alcohol 10 can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 80° C.

Preferred conditions are $CF_3COOH$ in aqueous acetonitrile at 80° C. for 3 hours.

Step C: Selective protection of the amino group of amino alcohol 10 can be effected by treatment with di-tert-butyl carbonate in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF or TBME.

Preferred conditions are N,N-diisopropylethylamine in THF at room temperature overnight.

Step D: Reduction of the olefinic bond of 11 without concomitant cleavage of the aryl-bromine bond can be accomplished by hydrogenation with hydrogen under normal or elevated pressure with a catalyst such as $PtO_2$ or Pt/C in solvents such as MeOH, EtOH, $H_2O$, dioxane, THF, HOAc, EtOAc $CH_2Cl_2$, $CHCl_3$, DMF or mixtures thereof.

Preferred conditions are 10% platinum on charcoal in MeOH at room temperature for 3 hours.

Step E: Oxidation of the alcohol 12 to the corresponding aldehyde 13 can be accomplished using DMSO-derived oxidation reagents, e.g. DMSO activated by the use of oxalyl chloride with subsequent treatment with triethylamine according to the method of Swern, or DMSO activated by use of sulphur trioxide-pyridine complex in the presence of triethylamine according to the method of Doering.

Preferred conditions are sulphur trioxide-pyridine complex and triethylamine in DMSO at a temperature between 0° C. and room temperature for 30 min.

Step F: Nucleophilic addition of a methyl group to aldehyde 13 can be accomplished by reaction with an organometallic reagent such as methylmagnesium chloride, methylmagnesium bromide, methylmagnesium iodide or methyllithium. The reaction is performed in ethereal solvents such as diethyl ether, dioxane, THF or TBME.

Preferred conditions are methylmagnesium bromide in a mixture of THF and diethyl ether at 0° C. and then at room temperature for 4 hours. The reaction affords alcohol 14 as a mixture of epimers which need not be separated at this stage.

Step G: Protection of alcohol 14 as a cyclic aminal can be accomplished by treatment with 2,2-dimethoxypropane in the presence of a catalytic amount of an organic acid such as p-toluenesulphonic acid or camphorsulphonic acid. The reaction can be performed using excess 2,2-dimethoxypropane as solvent, or in the presence of additional non-protic co-solvents such as halogenated solvents such as dichloromethane or 1,2-dichloroethane or ethereal solvents such as diethyl ether, dioxane, THF or TBME. The reaction can be performed at room temperature or at an elevated temperature such as the reflux temperature of the solvent.

Preferred conditions are p-toluenesulphonic acid in dichloromethane at room temperature overnight.

The reaction affords epimeric products 15 & 16 which can be readily separated by chromatography at this stage.

Step H: C—N bond formation to afford imine 17 can be accomplished by coupling reaction between aryl bromide 15 and diphenylmethanimine in the presence of a palladium or copper catalyst, a ligand and a base in solvents such as dioxane, DME, THF, toluene, and DMF at elevated temperatures.

Preferred conditions are $Pd_2(dba)_3$, BINAP and sodium tert-butoxide in toluene at 100° C. overnight.

Step I: Deprotection of imine 17 to afford aniline 18 can be accomplished by hydrogenation with hydrogen under normal or elevated pressure or by transfer hydrogenation using ammonium formiate or cyclohexadiene as hydrogen source with a catalyst such as $PtO_2$, Pt/C or Pd/C in solvents such as MeOH, EtOH, $H_2O$, dioxane, THF, HOAc, EtOAc $CH_2Cl_2$, $CHCl_3$, DMF or mixtures thereof.

Preferred conditions are 10% palladium on charcoal and ammonium formate in MeOH at 60° C. for 1 hour.

Aryl bromide 16 can be converted to aniline 19 following a similar sequence of reaction steps H and I.

Scheme 3

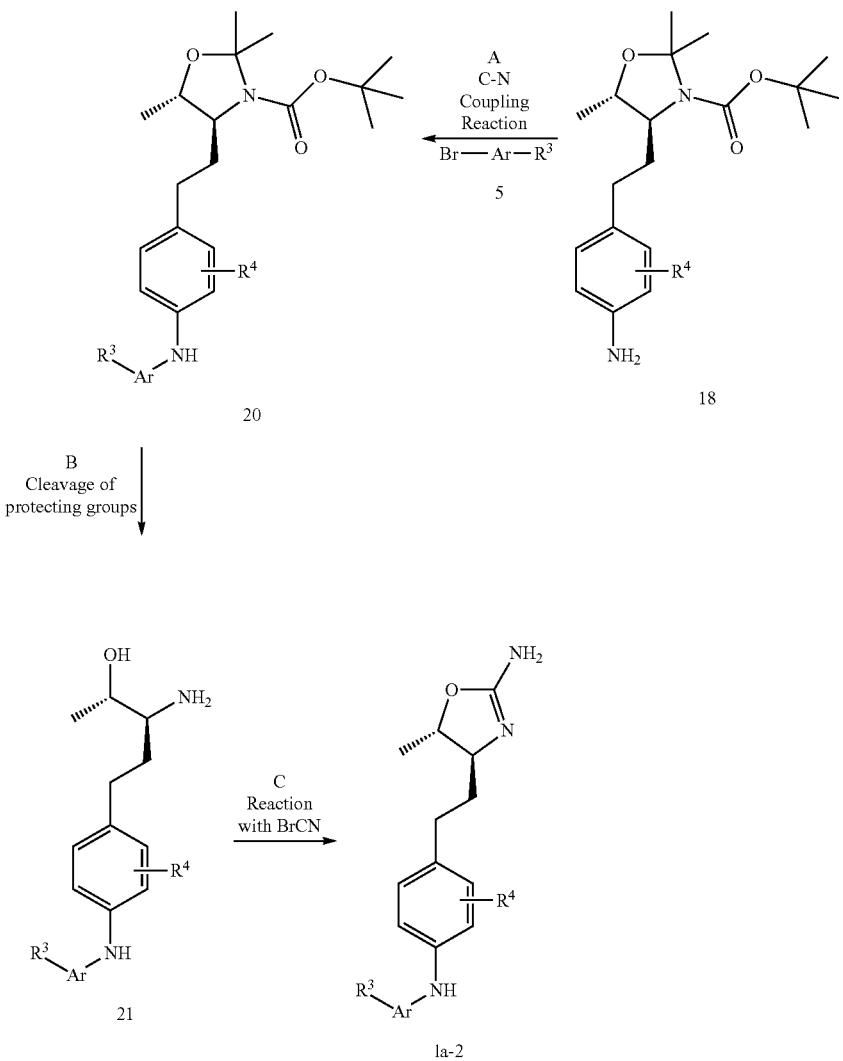

-continued

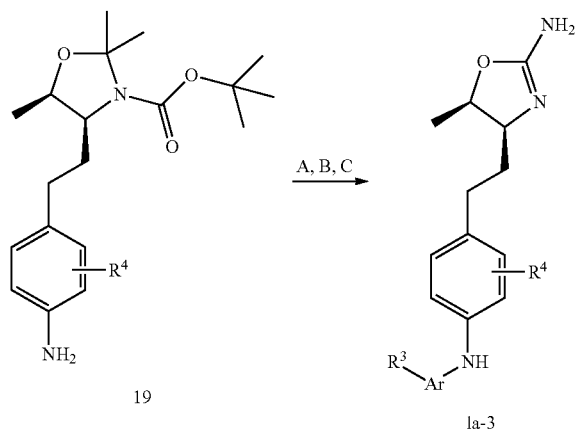

19

1a-3

Step A: C—N bond formation can be accomplished by treatment of aryl amine 18 with aryl bromide 5 in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium chloroform complex, catalytic 9,9-dimethyl-4,5-bis(diphenylphosphino)xanthene (xantphos) and caesium carbonate in dioxane in a sealed tube heated at 110° C. overnight according to a modification of the procedure of van Leeuwen and co-workers (*Tetrahedron. Lett.* 1999, 40, 3789-3790).

Alternative preferred conditions are catalytic palladium(II) acetate, catalytic 2,2'-bis(diphenylphosphino)-1,1'-binaphthalene (BINAP) and potassium carbonate in toluene in a sealed tube heated at 110° C. for 1 hour according to the procedure of Dommisse and co-workers (*Tetrahedron* 2001, 57, 7027-7034).

Step B: Simultaneous cleavage of the amino alcohol protecting groups of 20 can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 80° C.

Preferred conditions are $CF_3COOH$ in aqueous acetonitrile at 80° C. for 2 hours or 4 N HCl in dioxane and THF at 60° C. for 2 hours.

Step C: Cyclisation of the amino alcohol 21 to the corresponding 2-aminooxazoline Ia-2 can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight followed by treatment with aqueous ammonia solution at room temperature for 1 hour.

Preferred conditions are methanol as solvent and sodium acetate as base at r.t. overnight followed by treatment with aqueous ammonia solution at room temperature for 1 hour. Amine 19 can be converted to 2-aminooxazoline Ia-3 following a similar sequence of reaction steps A, B and C.

Scheme 4

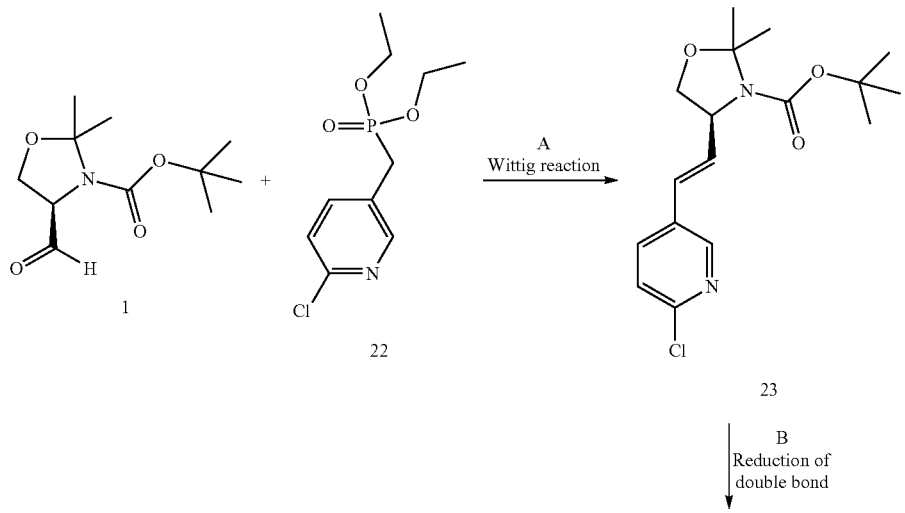

B
Reduction of double bond

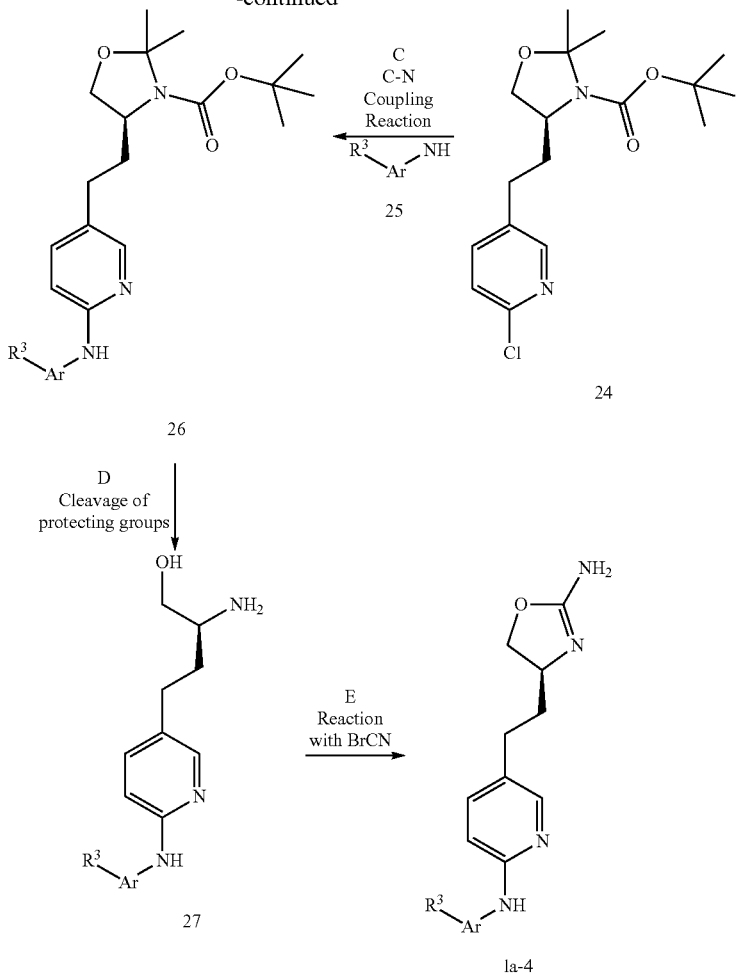

Step A: Wittig reaction between aldehyde 1 (CAS 95715-87-0) and phosphonate ester 22 (6-chloro-pyridin-3-ylmethyl)-phosphonic acid diethyl ester [CAS 561066-65-7]) can be accomplished by using a base such as NaH, KOtBu, NaOMe, NaOEt, n-BuLi, LiHMDS, NaHMDS, KHMDS, LDA in a solvent such as THF, dioxane, acetonitrile, 1,2-dimethoxyethane, DMF, benzene, toluene or mixtures thereof at temperatures from −78° C. to 80° C. for 15 min-8 hrs and if appropriate optional addition of a crown ether for glide generation and then condensing the ylide with the carbonyl compound in the same solvent at a temperature between 0 and 80° C. for 1-24 hrs. Alternatively, the base, the carbonyl compound and the optional crown ether can be added to the reaction mixture at the same time without preformation of the ylide at temperatures from −78° C. to 80° C.

Preferred conditions are ylide formation at −78° C. using LDA (prepared in situ from treatment of N,N-diisopropylamine with n-BuLi) as base and THF as solvent, reacting the phosphonic acid ester for 1 hour at −78° C., and then condensation with the carbonyl component warming to room temperature overnight.

Step B: Reduction of the alkene 23 without concomitant reduction of the chloro group can be effected by hydrogenation with hydrogen under normal or elevated pressure with a catalyst such as $PtO_2$ or Pt—C in solvents such as MeOH, EtOH, $H_2O$, dioxane, THF, HOAc, EtOAc $CH_2Cl_2$, $CHCl_3$, DMF or mixtures thereof.

Preferred conditions are hydrogenation in the presence of platinum on charcoal as catalyst with MeOH as solvent at room temperature and atmospheric pressure for 15 minutes.

Step C: C—N bond formation can be accomplished by treatment of aryl chloride 24 with aryl amine 25 in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium chloroform complex, catalytic 9,9-dimethyl-4,5-bis(diphenylphosphino)xanthene (xantphos) and caesium carbonate in dioxane in a sealed tube heated at 100° C. overnight according to a modification of the procedure of van Leeuwen and co-workers (*Tetrahedron. Lett.* 1999, 40, 3789-3790).

Step D: Simultaneous cleavage of the amino alcohol protecting groups of 26 can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 80° C.

Preferred conditions are $CF_3COOH$ in aqueous acetonitrile at 80° C. for 2 hours or 4 N HCl in dioxane and THF at 60° C. for 2 hours.

Step E: Cyclisation of the amino alcohol 27 to the corresponding 2-aminooxazoline Ia-4 can be accomplished by treatment with cyanogen bromide in THF as solvent and K$_2$CO$_3$ as base at r.t. overnight, or by treatment with cyanogen bromide in methanol as solvent and sodium acetate as base at 0° C. to r.t. overnight followed by treatment with aqueous ammonia solution at room temperature for 1 hour.

Preferred conditions are methanol as solvent and sodium acetate as base at r.t. overnight followed by treatment with aqueous ammonia solution at room temperature for 1 hour.

Step A: Addition of a trifluoromethyl group to aromatic aldehyde 28 can be accomplished by treatment with (trifluoromethyl)trimethylsilane in the presence of a source of fluoride ion such as tetrabutylammonium fluoride.

Preferred conditions are using THF as solvent at 0° C. for 30 minutes and then at room temperature for 2 hours.

Step B: Conversion of alcohol 29 to the corresponding triflate ester 30 can be can be accomplished by deprotonation

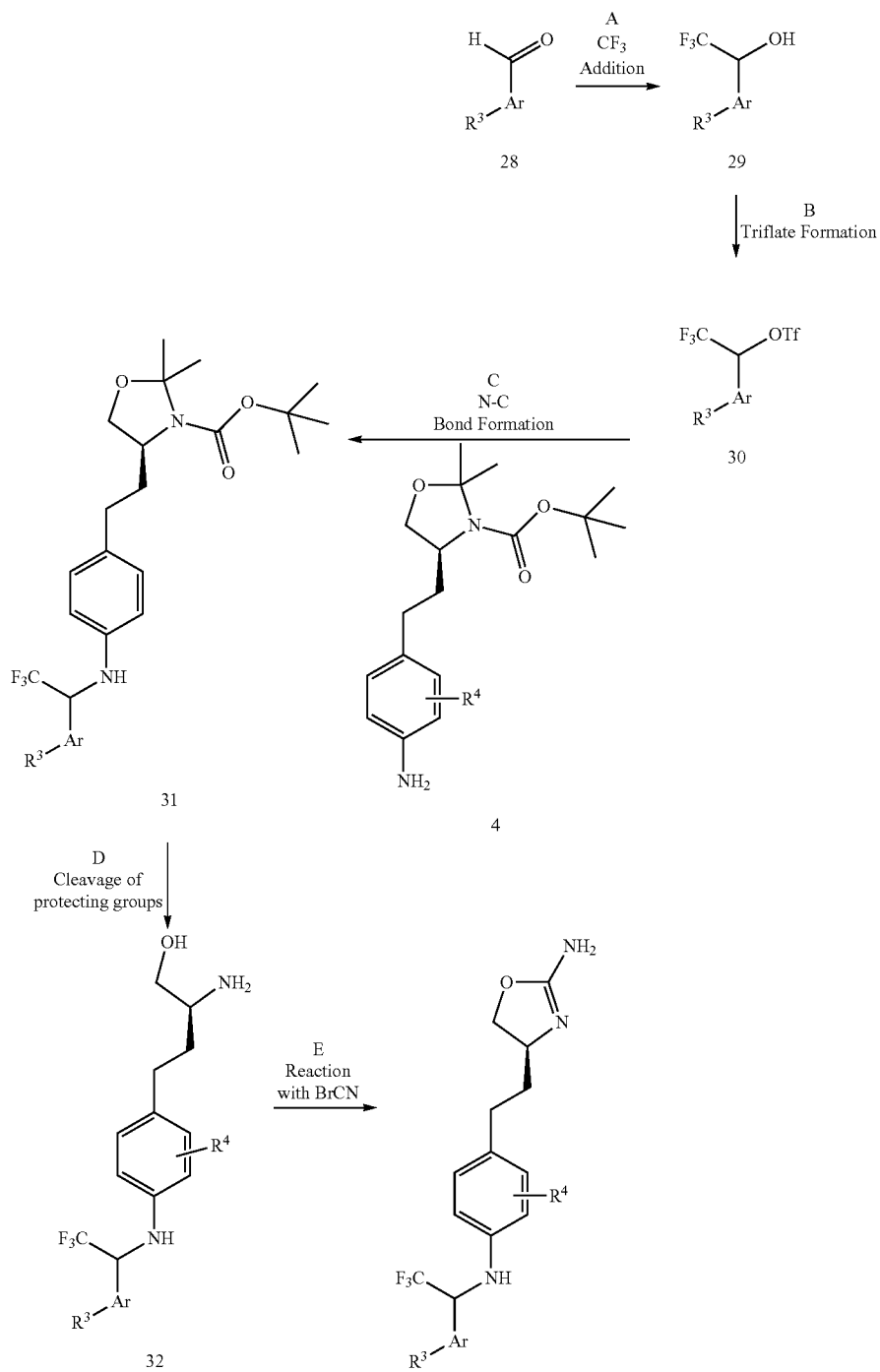

Scheme 5 with a base such as NaH, KOtBu, n-BuLi, LiHMDS, NaHMDS, KHMDS or LDA in non-protic organic solvents such as THF, dioxane, 1,2-dimethoxyethane, DMF, benzene, toluene or mixtures thereof at temperatures from −78° C. to 80° C. for 15 min-2 hrs followed by treatment with trifluoromethane sulfonyl chloride.

Preferred conditions are deprotonation at room temperature for 30 min using sodium hydride as base and diethyl ether as solvent, followed by treatment with trifluoromethane sulfonyl chloride at room temperature for 15 min.

Step C: C—N bond formation can be accomplished by treatment of triflate 30 with aryl amine 4 in the presence of a base such as NaH, KOtBu, n-BuLi, LiHMDS, NaHMDS, KHMDS or LDA in non-protic organic solvents such as THF, dioxane, 1,2-dimethoxyethane, DMF, benzene, toluene or mixtures thereof at temperatures from −78° C. to 80° C. for 15 min-2 hrs followed by treatment with trifluoromethane sulfonyl chloride.

Preferred conditions are deprotonation of amine 4 at room temperature for 15 min using sodium hydride as base and THF as solvent, followed by treatment with triflate 30 at room temperature overnight.

Step D: Simultaneous cleavage of the amino alcohol protecting groups of 31 can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 80° C.

Preferred conditions are $CF_3COOH$ in aqueous acetonitrile at 80° C. for 2 hours or 4 N HCl in dioxane and THF at 60° C. for 2 hours.

Step E: Cyclisation of the amino alcohol 32 to the corresponding 2-aminooxazoline Ib-1 can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight followed by treatment with aqueous ammonia solution at room temperature for 1 hour.

Preferred conditions are methanol as solvent and sodium acetate as base at r.t. overnight followed by treatment with aqueous ammonia solution at room temperature for 1 hour.

EXPERIMENTAL

Example 1

(S)-4-(4-(Quinolin-8-ylamino)phenethyl)-4,5-dihydrooxazol-2-amine

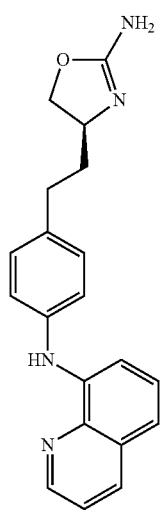 [SMILES: NC1=N[C@@H](CCc2ccc(Nc3cccc4cccnc34)cc2)CO1]

The title compound was obtained in analogy to example 13 using 8-bromo-quinoline instead of bromobenzene in step a). Yellow solid. MS (ISP): 333.2 ([M+H]$^+$).

Example 2

(S)-4-(4-(Naphthalen-1-ylamino)phenethyl)-4,5-dihydrooxazol-2-amine

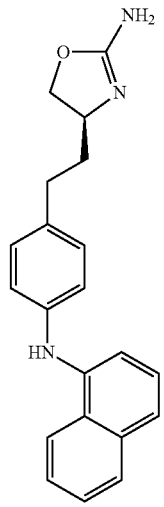 [SMILES: NC1=N[C@@H](CCc2ccc(Nc3cccc4ccccc34)cc2)CO1]

The title compound was obtained in analogy to example 13 using 1-bromo-naphthalene instead of bromobenzene in step a). Off-white solid. MS (ISP): 332.2 ([M+H]$^+$).

Example 3

(S)-4-(4-(5-Fluoropyridin-2-ylamino)phenethyl)-4,5-dihydrooxazol-2-amine

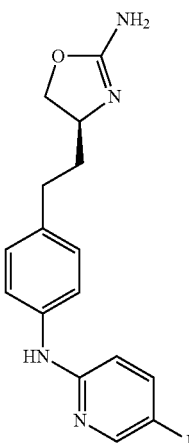

The title compound was obtained in analogy to example 13 using 2-bromo-5-fluoropyridine instead of bromobenzene in step a). Light yellow oil. MS (ISP): 301.2 ([M+H]$^+$).

Example 4

(S)-4-(4-(6-Methylquinolin-8-ylamino)phenethyl)-4,5-dihydrooxazol-2-amine

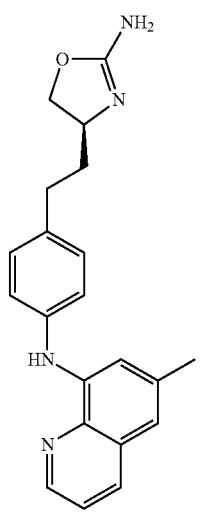 [SMILES: Cc1cc(Nc2ccc(CC[C@H]3COC(N)=N3)cc2)c2ncccc2c1]

The title compound was obtained in analogy to example 13 using 8-bromo-6-methyl-quinoline instead of bromobenzene in step a). Yellow solid. MS (ISP): 347.2 ([M+H]$^+$).

Example 5

(S)-4-(4-(8-Chloronaphthalen-1-ylamino)phenethyl)-4,5-dihydrooxazol-2-amine

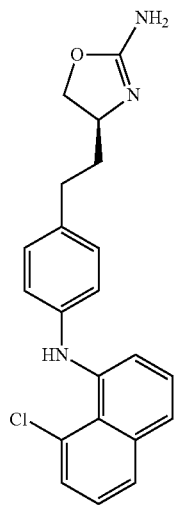 [SMILES: NC1=N[C@@H](CCc2ccc(Nc3cccc4cccc(Cl)c34)cc2)CO1]

The title compound was obtained in analogy to example 13 using 1-bromo-8-chloro-naphthalene instead of bromobenzene in step a). Off-white solid. MS (ISP): 368.1 ([{$^{37}$Cl}M+H]$^+$), 366.1 ([{$^{35}$Cl}M+H]$^+$).

Example 6

(S)-4-{2-[4-(4-Chloro-phenylamino)-phenyl]-ethyl}-4,5-dihydro-oxazol-2-ylamine

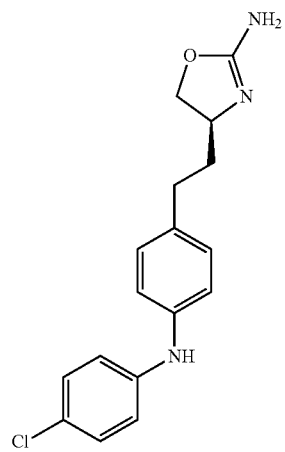 [SMILES: NC1=N[C@@H](CCc2ccc(Nc3ccc(Cl)cc3)cc2)CO1]

a) (S)-2,2-Dimethyl-4-[(E)-2-(4-nitro-phenyl)-vinyl]-oxazolidine-3-carboxylic acid tert-butyl ester To a stirred solution of diisopropylamine (10.9 ml) in THF (350 ml) cooled to −78° C. was added dropwise a solution of n-butyllithium in hexane (48.3 ml, 1.6 M). The cooling bath was removed and the reaction mixture was allowed to warm up to 10° C. before being re-cooled to −78° C. A solution of (4-nitro-benzyl)-phosphonic acid diethyl ester (16.3 g, CAS 2609-49-6) in THF (300 ml) was then added dropwise and the reaction mixture stirred at −78° C. for 1 hour. A solution of (R)-4-formyl-2,2-dimethyl-oxazolidine-3-carboxylic acid tert-butyl ester (15.0 g, CAS 95715-87-0) in THF (250 ml) was then added dropwise over 1 hour and the mixture was then allowed to warm to room temperature overnight. The mixture was then diluted with ethyl acetate and acidified by addition of 2 N aq. hydrochloric acid. The mixture was then washed sequentially with water and saturated brine. The organic phase was separated and dried over sodium sulphate and concentrated in vacuo. The reside was purified by column chromatography (SiO$_2$; gradient: heptane/EtOAc) to give (S)-2,2-dimethyl-4-[(E)-2-(4-nitro-phenyl)-vinyl]-oxazolidine-3-carboxylic acid tert-butyl ester (15.9 g, 77%) as a yellow oil. MS (EI): 333 ([M−CH$_3$]$^+$), 292 ([M−C$_4$H$_8$]$^+$), 277 ([M−CH$_3$—C$_4$H$_8$]$^+$), 57 ([C$_4$H$_9$]$^+$).

b) (S)-4-[2-(4-Amino-phenyl)-ethyl]-2,2-dimethyl-oxazolidine-3-carboxylic acid tert-butyl ester To a stirred suspension of (S)-2,2-dimethyl-4-[(E)-2-(4-nitro-phenyl)-vinyl]-oxazolidine-3-carboxylic acid tert-butyl ester (12.0 g) in methanol (500 ml) were added ammonium formate (32.6 g) and palladium on charcoal (1.83 g, 10 wt %) and the mixture was heated at 50° C. for 1 hour. The mixture was then cooled to room temperature, filtered through celite and the filtrate was concentrated in vacuo. The residue was then taken up in ethyl acetate and washed with water. The phases were separated and the organic phase was dried over sodium sulphate and concentrated in vacuo. The reside was purified by column chromatography (SiO$_2$; gradient: heptane/EtOAc) to give (S)-4-[2-(4-amino-phenyl)-ethyl]-2,2- dimethyl-oxazolidine-3-carboxylic acid tert-butyl ester (8.72 g, 79%) as a yellow oil. MS (ISP): 321.4 ([M+H]$^+$).

c) (S)-4-{2-[4-(4-Chloro-phenylamino)-phenyl]-ethyl}-2,2-dimethyl-oxazolidine-3-carboxylic acid tert-butyl ester In a pressure tube, (S)-4-[2-(4-amino-phenyl)-ethyl]-2,2-dimethyl-oxazolidine-3-carboxylic acid tert-butyl ester (0.3 g), 1-bromo-4-chlorobenzene (215 mg) and cesium carbonate (458 mg) were combined with dioxane (3 ml) to give a yellow suspension. The mixture was degassed by bubbling through argon for several minutes. Xantphos (32.5 mg) and tris(dibenzylideneacetone)dipalladium chloroform complex (29.1 mg) were then added and the tube was sealed. The reaction mixture was stirred at 110° C. overnight. The reaction mixture was then cooled to room temperature and concentrated in vacuo. The residue was purified by flash chromatography (SiO$_2$; gradient: 0% to 100% EtOAc in hexane) to afford (S)-4-{2-[4-(4-chloro-phenylamino)-phenyl]-ethyl}-2,2-dimethyl-oxazolidine-3-carboxylic acid tert-butyl ester (228 mg, 57%) as a yellow oil. MS (EI): 432 ({$^{37}$Cl}M$^+$), 430 ({$^{35}$Cl}M+H—OH$^+$), 376 ({$^{37}$Cl}[M–C$_4$H$_8$]$^+$), 374 ({$^{35}$Cl}[M–C$_4$H$_8$]), 231 ({$^{37}$Cl}[ClC$_6$H$_4$NHC$_6$H$_4$CH=CH$_2$]$^+$), 229 ({$^{35}$Cl}[ClC$_6$H$_4$NHC$_6$H$_4$CH=CH$_2$]$^+$), 57 ([C$_4$H$_9$]$^+$).

d) (S)-2-Amino-4-[4-(4-chloro-phenylamino)-phenyl]-butan-1-ol

To a solution of (S)-4-{2-[4-(4-chloro-phenylamino)-phenyl]-ethyl}-2,2-dimethyl-oxazolidine-3-carboxylic acid tert-butyl ester (220 mg) in THF (3 ml) in a pressure tube was added HCl solution (2.55 ml, 4 M solution in dioxane). The tube was sealed and the reaction mixture was shaken at 60° C. for 2 hours. The mixture was then cooled to room temperature and poured into 1 M aq. NaOH and extracted with EtOAc. The phases were then separated and the organic phase was dried over sodium sulphate and concentrated in vacuo to afford (S)-2-amino-4-[4-(4-chloro-phenylamino)-phenyl]-butan-1-ol (148 mg, quant.) as a yellow oil which was used in the next step without further purification. MS (ISP): 293.0 ([{$^{37}$Cl}M+H]$^+$), 291.1 ([{$^{35}$Cl}M+H]$^+$).

e) (S)-4-{2-[4-(4-Chloro-phenylamino)-phenyl]-ethyl}-4,5-dihydro-oxazol-2-ylamine To a stirred suspension of (S)-2-amino-4-[4-(4-chloro-phenylamino)-phenyl]-butan-1-ol (210 mg) and sodium acetate (121 mg) in methanol (5 ml) was added dropwise a solution of cyanogen bromide (68 mg) in methanol (0.3 ml). The resulting pale yellow solution was then stirred at room temperature for 16 h. Aqueous ammonia solution (0.4 ml, 25%) was added dropwise and stirring was continued for a further hour. The mixture was then concentrated in vacuo and the residue was purified by column chromatography (Isolute® Flash-NH$_2$ from Separtis; gradient: heptane/EtOAc/MeOH) to give (S)-4-{2-[4-(4-chloro-phenylamino)-phenyl]-ethyl}-4,5-dihydro-oxazol-2-ylamine (74 mg, 48%) as a yellow solid. MS (ISP): 318.1 ([{$^{37}$Cl}M+H]$^+$), 316.1 ([{$^{35}$Cl}M+H]$^+$).

Example 7

(S)-4-{2-[4-(4-Chloro-2-fluoro-phenylamino)-phenyl]-ethyl}-4,5-dihydro-oxazol-2-ylamine

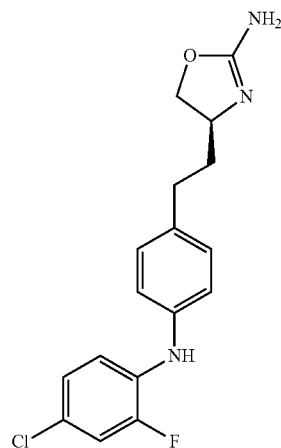 [SMILES: NC1=N[C@@H](CCc2ccc(Nc3ccc(Cl)cc3F)cc2)CO1]

The title compound was obtained in analogy to example 6 using 1-bromo-4-chloro-2-fluorobenzene instead of 1-bromo-4-chlorobenzene in step c). Off-white solid. MS (ISP): 336.1 ([{$^{37}$Cl}M+H]$^+$), 334.1 ([{$^{35}$Cl}M+H]$^+$).

Example 8

(S)-4-{2-[4-(4-Trifluoromethyl-phenylamino)-phenyl]-ethyl}-4,5-dihydro-oxazol-2-ylamine

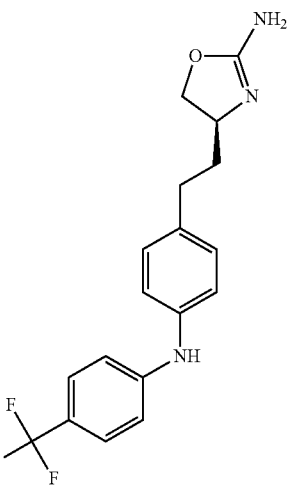

The title compound was obtained in analogy to example 6 using 1-bromo-4-(trifluoromethyl)benzene instead of 1-bromo-4-chlorobenzene in step c). Off-white solid. MS (ISP): 350.1 ([M+H]$^+$).

Example 9

(S)-4-{2-[4-(4-Methoxy-phenylamino)-phenyl]-ethyl}-4,5-dihydro-oxazol-2-ylamine

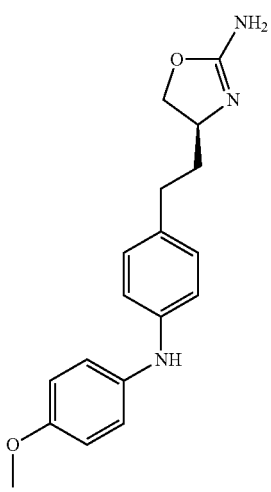 [SMILES: COc1ccc(Nc2ccc(CC[C@H]3COC(N)=N3)cc2)cc1]

The title compound was obtained in analogy to example 6 using 1-bromo-4-methoxybenzene instead of 1-bromo-4-chlorobenzene in step c). Off-white solid. MS (ISP): 312.2 ([M+H]$^+$).

Example 10

(S)-4-(4-(3-Methyl-4-(trifluoromethoxy)phenylamino)phenethyl)-4,5-dihydrooxazol-2-amine

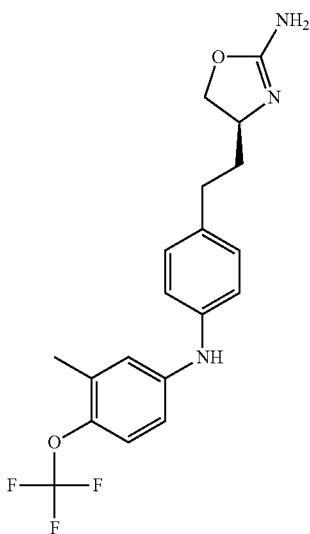 [SMILES: Cc1cc(Nc2ccc(CC[C@H]3COC(N)=N3)cc2)ccc1OC(F)(F)F]

The title compound was obtained in analogy to example 6 using 4-bromo-2-methyl-1-(trifluoromethoxy)benzene instead of 1-bromo-4-chlorobenzene in step c). Off-white solid. MS (ISP): 380.2 ([M+H]$^+$).

Example 11

{4-[2-((S)-2-Amino-4,5-dihydro-oxazol-4-yl)-ethyl]-phenyl}-(5-trifluoromethyl-pyridin-2-yl)-amine

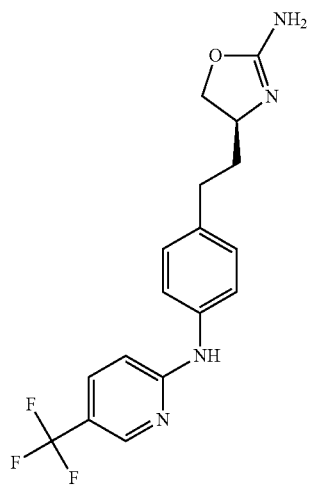 [SMILES: NC1=N[C@@H](CCc2ccc(Nc3ccc(C(F)(F)F)cn3)cc2)CO1]

a) (S)-2,2-Dimethyl-4-{2-[4-(5-trifluoromethyl-pyridin-2-ylamino)-phenyl]-ethyl}-oxazolidine-3-carboxylic acid tert-butyl ester In a pressure tube, (S)-4-[2-(4-amino-phenyl)-ethyl]-2,2-dimethyl-oxazolidine-3-carboxylic acid tert-butyl ester (100 mg), 2-chloro-5-(trifluoromethyl)pyridine (57 mg) and potassium carbonate (431 mg) were combined with toluene (1 ml) to give a yellow solution. The mixture was degassed by bubbling through argon for several minutes. BINAP (12 mg) and palladium(II)acetate (2 mg) were then added and the tube was sealed. The reaction mixture was stirred at 110° C. for 1 hour. The reaction mixture was then cooled to room temperature and concentrated in vacuo. The residue was purified by flash chromatography (SiO$_2$; gradient: 0% to 40% EtOAc in hexane) to afford (S)-2,2-dimethyl-4-{2-[4-(5-trifluoromethyl-pyridin-2-ylamino)-phenyl]-ethyl}-oxazolidine-3-carboxylic acid tert-butyl ester (55 mg, 38%) as a yellow amorphous solid. MS (ISP): 466.3 ([M+H]$^+$), 410.2 ([M+H—C$_4$H$_8$]$^+$), 366.2 ([M+H—C$_4$H$_8$—CO$_2$]$^+$).

b) (S)-2-Amino-4-[4-(5-trifluoromethyl-pyridin-2-ylamino)-phenyl]-butan-1-ol

To a solution of (S)-2,2-dimethyl-4-{2-[4-(5-trifluoromethyl-pyridin-2-ylamino)-phenyl]-ethyl}-oxazolidine-3-carboxylic acid tert-butyl ester (54 mg) in acetonitrile (0.5 ml) were added water (1.5 ml) and trifluoroacetic acid (0.071 ml). The mixture was heated at 80° C. for 2 h. The mixture was then cooled to room temperature and diluted with ethyl acetate. The resulting mixture was washed sequentially with 1 N aq. sodium hydroxide solution and saturated brine, the phases were then separated and the organic phase was dried over sodium sulphate and concentrated in vacuo to afford (S)-2-amino-4-[4-(5-trifluoromethyl-pyridin-2-ylamino)-phenyl]-butan-1-ol (38 mg, quant.) as a yellow oil which was used in the next step without further purification. MS (ISP): 326.3 ([M+H]$^+$).

c) {4-[2-((S)-2-Amino-4,5-dihydro-oxazol-4-yl)-ethyl]-phenyl}-(5-trifluoromethyl-pyridin-2-yl)-amine The title compound was obtained in analogy to example 6 step e) using (S)-2-amino-4-[4-(5-trifluoromethyl-pyridin-2-ylamino)-phenyl]-butan-1-ol instead of (S)-2-amino-4-[4-(4-chloro-phenylamino)-phenyl]-butan-1-ol. White solid. MS (ISP): 351.2 ([M+H]$^+$).

Example 12

(S)-6,6'-(4-(2-(2-Amino-4,5-dihydrooxazol-4-yl)ethyl)phenylazanediyl)dinicotinonitrile

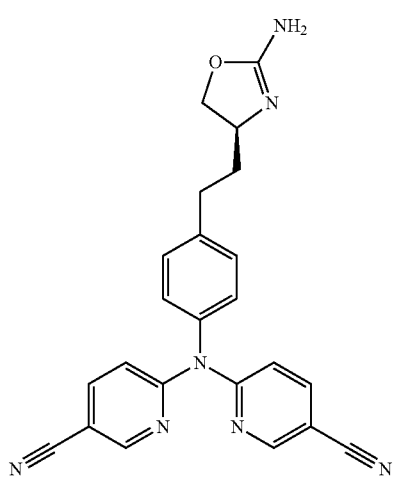 [SMILES: N#Cc1ccc(N(c2ccc(CC[C@H]3COC(N)=N3)cc2)c2ccc(C#N)cn2)nc1]

The title compound was obtained in analogy to example 11 using 6-chloronicotinonitrile instead of 2-chloro-5-(trifluoromethyl)pyridine in step a). Yellow amorphous solid. MS (ISP): 410.2 ([M+H]$^+$).

Example 13

(S)-4-[2-(4-Phenylamino-phenyl)-ethyl]-4,5-dihydro-oxazol-2-ylamine

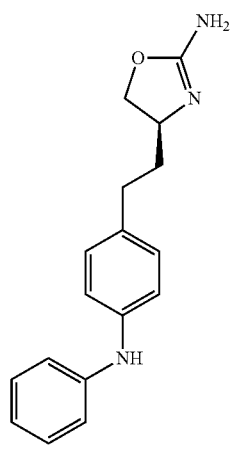 [SMILES: NC1=N[C@@H](CCc2ccc(Nc3ccccc3)cc2)CO1]

a) (S)-2,2-Dimethyl-4-[2-(4-phenylamino-phenyl)-ethyl]-oxazolidine-3-carboxylic acid tert-butyl ester The title compound was obtained in analogy to example 6 steps a)-c) using bromobenzene instead of 1-bromo-4-chlorobenzene in step c). Yellow oil. MS (ISP): 397.2 ([M+H]$^+$), 297.3 ([M+H—C$_4$H$_8$—CO$_2$]$^+$).

b) (S)-2-Amino-4-(4-phenylamino-phenyl)-butan-1-ol

The title compound was obtained in analogy to example 11 step b) using (S)-2,2-dimethyl-4-[2-(4-phenylamino-phenyl)-ethyl]-oxazolidine-3-carboxylic acid tert-butyl ester in place of (S)-2,2-dimethyl-4-{2-[4-(5-trifluoromethyl-pyridin-2-ylamino)-phenyl]-ethyl}-oxazolidine-3-carboxylic acid tert-butyl ester. Yellow solid. MS (ISP): 257.2 ([M+H]$^+$).

c) {4-[2-(S)-2-Amino-4,5-dihydro-oxazol-4-yl)-ethyl]-phenyl}-(5-trifluoromethyl-pyridin-2-yl)-amine The title compound was obtained in analogy to example 6 step e) using (S)-2-amino-4-(4-phenylamino-phenyl)-butan-1-ol instead of (S)-2-amino-4-[4-(4-chloro-phenylamino)-phenyl]-butan-1-ol. Off-white solid. MS (ISP): 282.2 ([M+H]$^+$).

Example 14

(S)-4-(4-(p-Tolylamino)phenethyl)-4,5-dihydrooxazol-2-amine

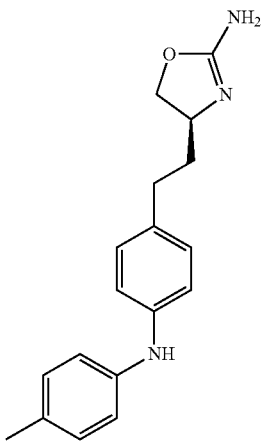 [SMILES: Cc1ccc(Nc2ccc(CC[C@H]3COC(N)=N3)cc2)cc1]

The title compound was obtained in analogy to example 13 using 1-bromo-4-methylbenzene instead of bromobenzene in step a). Off-white solid MS (ISP): 296.2 ([M+H]$^+$).

Example 15

{4-[2-((S)-2-Amino-4,5-dihydro-oxazol-4-yl)-ethyl]-phenyl}-(5-chloro-pyridin-2-yl)-amine

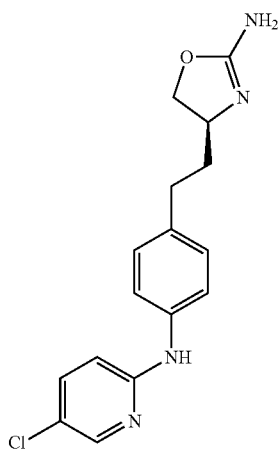 [SMILES: NC1=N[C@@H](CCc2ccc(Nc3ccc(Cl)cn3)cc2)CO1]

The title compound was obtained in analogy to example 13 using 2,5-dichloropyridine instead of bromobenzene in step a). Off-white solid MS (ISP): 319.1 ([{$^{37}$Cl}M+H]$^+$), 317.1 ([{$^{35}$Cl}M+H]$^+$).

Example 16

6-{4-[2-((S)-2-Amino-4,5-dihydro-oxazol-4-yl)-ethyl]-phenylamino}-nicotinonitrile

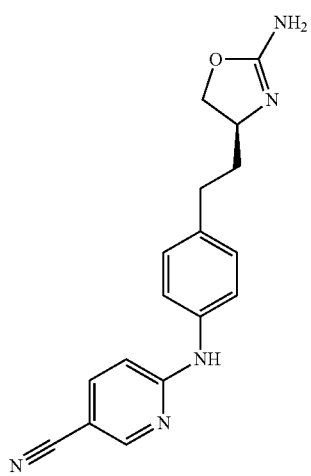 [SMILES: N#Cc1ccc(Nc2ccc(CC[C@H]3COC(N)=N3)cc2)nc1]

The title compound was obtained in analogy to example 13 using 6-chloronicotinonitrile instead of bromobenzene in step a). Off-white solid MS (ISP): 308.2 ([M+H]$^+$).

Example 17

(S)-4-(4-(6-(Trifluoromethyl)pyrimidin-4-ylamino) phenethyl)-4,5-dihydrooxazol-2-amine

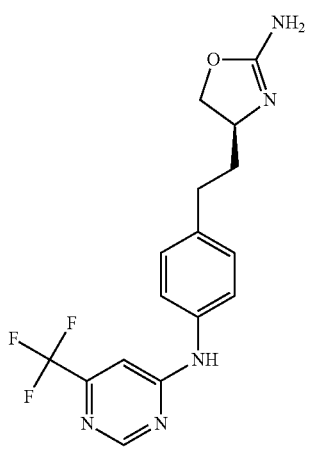 [SMILES: NC1=N[C@@H](CCc2ccc(Nc3cc(C(F)(F)F)ncn3)cc2)CO1]

The title compound was obtained in analogy to example 13 using 4-chloro-6-(trifluoromethyl)pyrimidine instead of bromobenzene in step a). White solid MS (ISP): 352.1 ([M+H]$^+$).

Example 18

{4-[2-((S)-2-Amino-4,5-dihydro-oxazol-4-yl)-ethyl]-phenyl}-(5-chloro-pyrimidin-2-yl)-amine

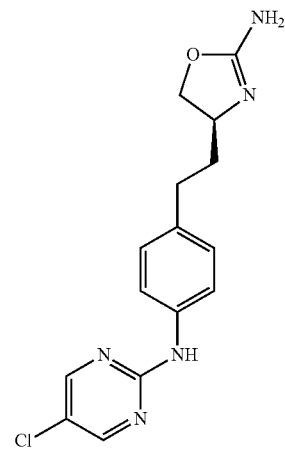 [SMILES: NC1=N[C@@H](CCc2ccc(Nc3ncc(Cl)cn3)cc2)CO1]

The title compound was obtained in analogy to example 13 using 2,5-dichloropyrimidine instead of bromobenzene in step a). White solid MS (ISP): 320.1 ([{$^{37}$Cl}M+H]$^+$), 318.1 ([{$^{35}$Cl}M+H]$^+$).

Example 19

(S)-4-(4-(3,4-Dichlorophenylamino)phenethyl)-4,5-dihydrooxazol-2-amine

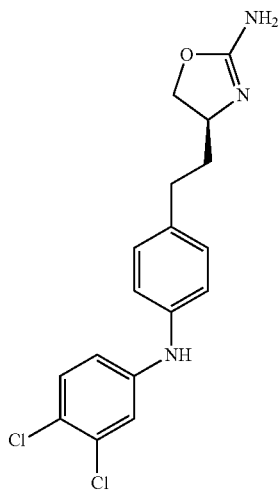 [SMILES: NC1=N[C@@H](CCc2ccc(Nc3ccc(Cl)c(Cl)c3)cc2)CO1]

The title compound was obtained in analogy to example 13 using 4-bromo-1,2-dichlorobenzene instead of bromobenzene in step a). Colourless amorphous solid MS (ISP): 354.1 ([$\{^{37}$Cl$\}$M+H]$^+$), 352.1 ([$\{^{37}$Cl$^{35}$Cl$\}$M+H]$^+$), 350.1 ([$\{^{35}$Cl$\}$M+H]$^+$).

Example 20

{4-[2-((S)-2-Amino-4,5-dihydro-oxazol-4-yl)-ethyl]-phenyl}-(5-fluoro-pyrimidin-2-yl)-amine

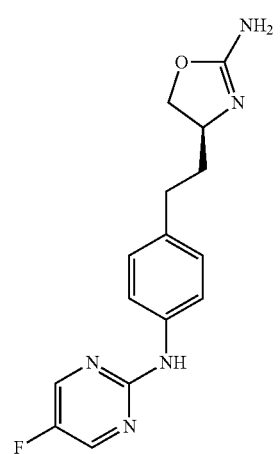 [SMILES: NC1=N[C@@H](CCc2ccc(Nc3ncc(F)cn3)cc2)CO1]

The title compound was obtained in analogy to example 13 using 2-chloro-5-fluoropyrimidine instead of bromobenzene in step a). White solid MS (ISP): 302.1 ([M+H]$^+$).

Example 21

{4-[2-((S)-2-Amino-4,5-dihydro-oxazol-4-yl)-ethyl]-phenyl}-(3-fluoro-pyridin-2-yl)-amine

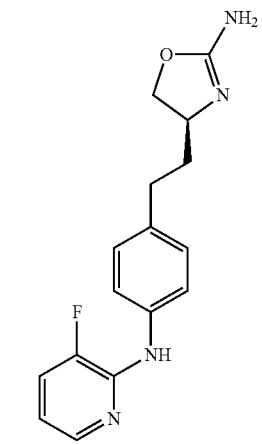 [SMILES: NC1=N[C@@H](CCc2ccc(Nc3ncccc3F)cc2)CO1]

The title compound was obtained in analogy to example 13 using 2-chloro-3-fluoropyridine instead of bromobenzene in step a). Colourless oil. MS (ISP): 301.1 ([M+H]$^+$).

Example 22

{4-[2-((S)-2-Amino-4,5-dihydro-oxazol-4-yl)-ethyl]-phenyl}-(4-fluoro-pyridin-2-yl)-amine

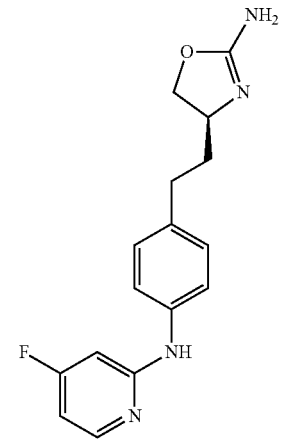 [SMILES: NC1=N[C@@H](CCc2ccc(Nc3cc(F)ccn3)cc2)CO1]

The title compound was obtained in analogy to example 13 using 2-chloro-4-fluoropyridine instead of bromobenzene in step a). Light yellow solid. MS (ISP): 301.1 ([M+H]$^+$).

Example 23

{4-[2-((S)-2-Amino-4,5-dihydro-oxazol-4-yl)-ethyl]-phenyl}-(4-trifluoromethyl-pyridin-2-yl)-amine

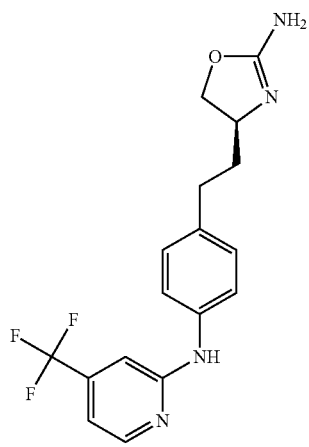 [SMILES: NC1=N[C@@H](CCc2ccc(Nc3cc(C(F)(F)F)ccn3)cc2)CO1]

The title compound was obtained in analogy to example 13 using 2-chloro-4-trifluoromethylpyridine instead of bromobenzene in step a). Light yellow solid. MS (ISP): 351.1 ([M+H]$^+$).

Example 24

{4-[2-((S)-2-Amino-4,5-dihydro-oxazol-4-yl)-ethyl]-phenyl}-(6-methyl-pyrimidin-4-yl)-amine

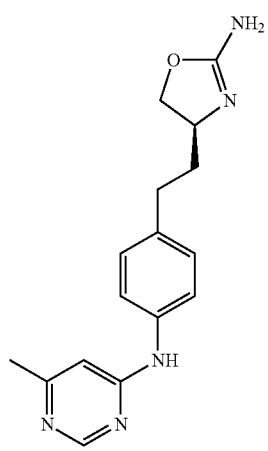

The title compound was obtained in analogy to example 13 using 4-chloro-6-methylpyrimidine instead of bromobenzene in step a). Light yellow solid. MS (ISP): 298.2 ([M+H]$^+$).

Example 25

{4-[2-((S)-2-Amino-4,5-dihydro-oxazol-4-yl)-ethyl]-phenyl}-(6-methyl-pyridin-2-yl)-amine

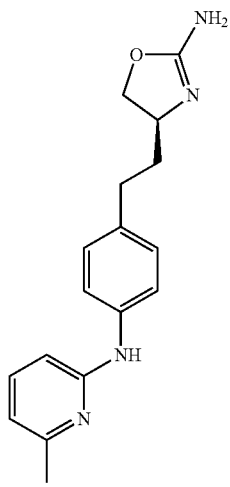 [SMILES: Cc1cccc(Nc2ccc(CC[C@H]3COC(N)=N3)cc2)n1]

The title compound was obtained in analogy to example 13 using 2-chloro-6-methylpyridine instead of bromobenzene in step a). Light yellow solid. MS (ISP): 297.2 ([M+H]$^+$).

Example 26

{4-[2-((S)-2-Amino-4,5-dihydro-oxazol-4-yl)-ethyl-]-phenyl}-(6-trifluoromethyl-pyridin-2-yl)-amine

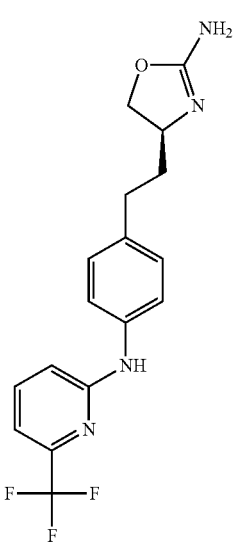 [SMILES: NC1=N[C@@H](CCc2ccc(Nc3cccc(C(F)(F)F)n3)cc2)CO1]

The title compound was obtained in analogy to example 13 using 2-chloro-6-trifluoromethylpyridine instead of bromobenzene in step a). Light yellow solid. MS (ISP): 351.1 ([M+H]$^+$).

Example 27

{4-[2-((S)-2-Amino-4,5-dihydro-oxazol-4-yl)-ethyl]-phenyl}-(6-chloro-pyrazin-2-yl)-amine

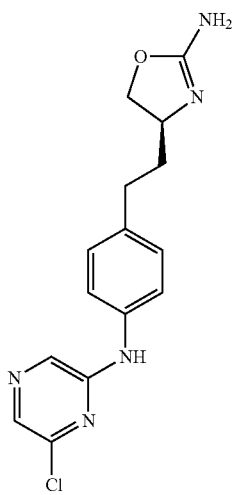 [SMILES: NC1=N[C@@H](CCc2ccc(Nc3cncc(Cl)n3)cc2)CO1]

The title compound was obtained in analogy to example 13 using 2,6-dichloro-pyrazine instead of bromobenzene in step a). Yellow solid. MS (ISP): 320.1 ([{$^{37}$Cl}M+H]$^+$), 318.1 ([{$^{35}$Cl}M+H]$^+$).

Example 28

{4-[2-((8)-2-Amino-4,5-dihydro-oxazol-4-yl)-ethyl]-phenyl}-(6-chloro-pyridin-2-yl)-amine

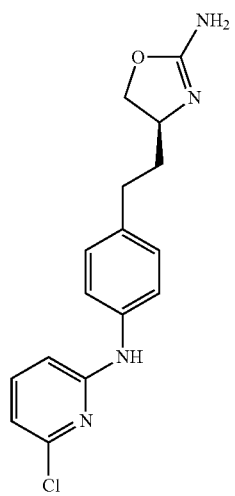 [SMILES: NC1=N[C@@H](CCc2ccc(Nc3cccc(Cl)n3)cc2)CO1]

The title compound was obtained in analogy to example 13 using 2,6-dichloro-pyridine instead of bromobenzene in step a). Colourless solid. MS (ISP): 319.1 ([{$^{37}$Cl}M+H]$^+$), 317.1 ([{$^{35}$Cl}M+H]$^+$).

Example 29

{4-[2-((8)-2-Amino-4,5-dihydro-oxazol-4-yl)-ethyl]-phenyl}-(5-methyl-pyridin-2-yl)-amine

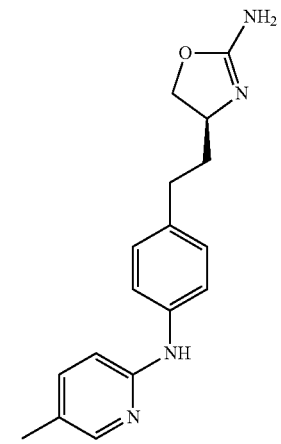 [SMILES: Cc1ccc(Nc2ccc(CC[C@H]3COC(N)=N3)cc2)nc1]

The title compound was obtained in analogy to example 13 using 2-chloro-5-methylpyridine instead of bromobenzene in step a). Colourless solid. MS (ISP): 297.2 ([M+H]$^+$).

Example 30

{4-[2-((S)-2-Amino-4,5-dihydro-oxazol-4-yl)-ethyl]-phenyl}-(5-methoxy-pyridin-2-yl)-amine

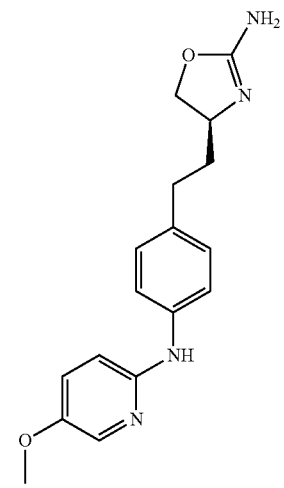 [SMILES: COc1ccc(Nc2ccc(CC[C@H]3COC(N)=N3)cc2)nc1]

The title compound was obtained in analogy to example 13 using 2-chloro-5-methoxypyridine instead of bromobenzene in step a). Colourless solid. MS (ISP): 313.2 ([M+H]$^+$).

Example 31

6-{4-[2-((S)-2-Amino-4,5-dihydro-oxazol-4-yl)-ethyl]-phenylamino}-pyrazine-2-carbonitrile

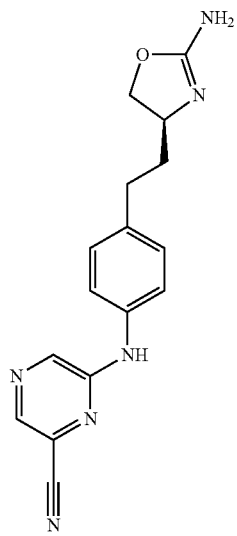 [SMILES: N#Cc1cncc(Nc2ccc(CC[C@H]3COC(N)=N3)cc2)n1]

The title compound was obtained in analogy to example 13 using 6-cyano-2-chloropyrazine instead of bromobenzene in step a). Colourless solid. MS (ISP): 309.1 ([M+H]$^+$).

Example 32

{4-[2-((S)-2-Amino-4,5-dihydro-oxazol-4-yl)-ethyl]-phenyl}-(6-chloro-pyrimidin-4-yl)-amine

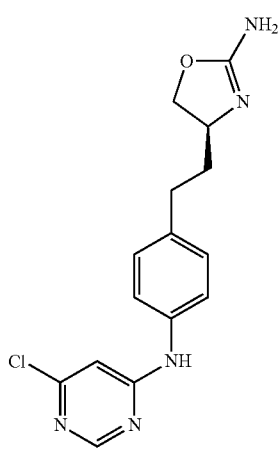 [SMILES: NC1=N[C@@H](CCc2ccc(Nc3cc(Cl)ncn3)cc2)CO1]

The title compound was obtained in analogy to example 13 using 4,6-dichloropyrimidine instead of bromobenzene in step a). White solid. MS (ISP): 320.1 ([{$^{37}$Cl}M+H]$^+$), 318.1 ([{$^{35}$Cl}M+H]$^+$).

Example 33

{4-[2-((S)-2-Amino-4,5-dihydro-oxazol-4-yl)-ethyl]-phenyl}-(6-methoxy-pyrimidin-4-yl)-amine

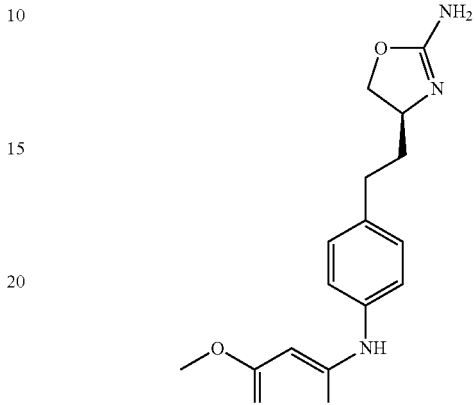

The title compound was obtained in analogy to example 13 using 4-chloro-6-methoxypyrimidine instead of bromobenzene in step a). White solid. MS (ISP): 314.2 ([M+H]$^+$).

Example 34

{4-[2-((S)-2-Amino-4,5-dihydro-oxazol-4-yl)-ethyl]-phenyl}-(2-methyl-pyrimidin-4-yl)-amine

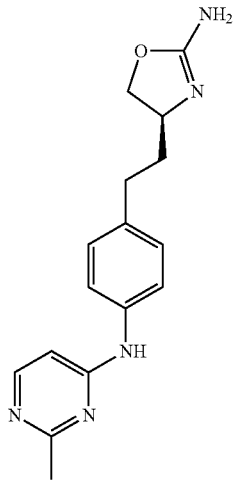 [SMILES: Cc1nccc(Nc2ccc(CC[C@H]3COC(N)=N3)cc2)n1]

The title compound was obtained in analogy to example 13 using 4-chloro-2-methylpyrimidine instead of bromobenzene in step a). Off-white solid. MS (ISP): 298.2 ([M+H]$^+$).

Example 35

(S)-4-(4-(Pyrimidin-4-ylamino)phenethyl)-4,5-dihydrooxazol-2-amine hydrochloride

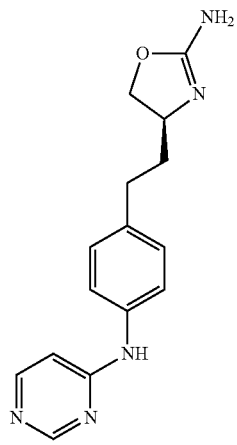 [SMILES: NC1=N[C@@H](CCc2ccc(Nc3ccncn3)cc2)CO1]

{4-[2-((S)-2-Amino-4,5-dihydro-oxazol-4-yl)-ethyl]-phenyl}-(6-chloro-pyrimidin-4-yl)-amine (16 mg, Example 32) was dissolved in methanol to give a colourless solution. The mixture was degassed by bubbling through argon for several minutes. 10% Palladium on charcoal (11 mg) was added and the reaction mixture was stirred under a hydrogen-filled balloon at room temperature for 2 hours. The reaction mixture was filtered through celite and the filtrate was concentrated in vacuo to afford (S)-4-(4-(pyrimidin-4-ylamino) phenethyl)-4,5-dihydrooxazol-2-amine hydrochloride (14 mg, 87%) as a white solid. MS (ISP): 284.2 ([M+H]$^+$).

Example 36

{4-[2-((S)-2-Amino-4,5-dihydro-oxazol-4-yl)-ethyl]-phenyl}-(4-methoxy-pyrimidin-2-yl)-amine

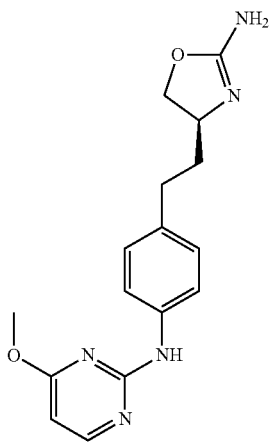 [SMILES: COc1ccnc(Nc2ccc(CC[C@H]3COC(N)=N3)cc2)n1]

The title compound was obtained in analogy to example 13 using 2-chloro-4-methoxypyrimidine instead of bromobenzene in step a). White solid. MS (ISP): 314.2 ([M+H]$^+$).

Example 37

{4-[2-((S)-2-Amino-4,5-dihydro-oxazol-4-yl)-ethyl]-phenyl}-(5-ethyl-pyrimidin-2-yl)-amine

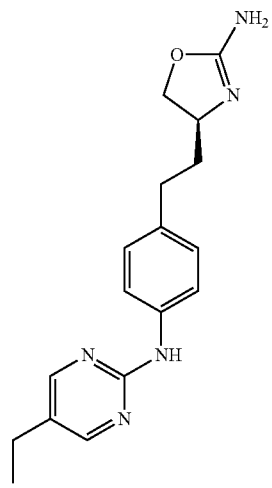 [SMILES: CCc1cnc(Nc2ccc(CC[C@H]3COC(N)=N3)cc2)nc1]

The title compound was obtained in analogy to example 13 using 2-chloro-5-ethylpyrimidine instead of bromobenzene in step a). White solid. MS (ISP): 312.2 ([M+H]$^+$).

Example 38

{4-[2-((8)-2-Amino-4,5-dihydro-oxazol-4-yl)-ethyl]-phenyl}-(5-methoxy-pyrimidin-2-yl)-amine

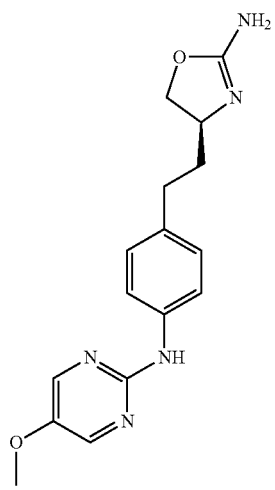 [SMILES: COc1cnc(Nc2ccc(CC[C@H]3COC(N)=N3)cc2)nc1]

The title compound was obtained in analogy to example 13 using 2-chloro-5-methoxypyrimidine instead of bromobenzene in step a). White solid. MS (ISP): 314.2 ([M+H]$^+$).

Example 39

5-{4-[2-((S)-2-Amino-4,5-dihydro-oxazol-4-yl)-ethyl]-phenylamino}-pyrazine-2-carbonitrile

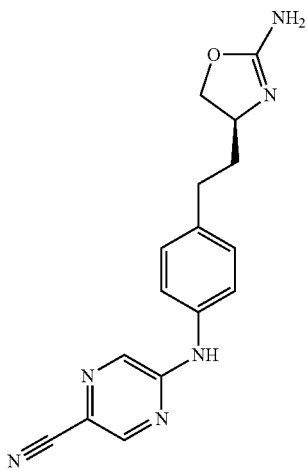 [SMILES: N#Cc1cnc(Nc2ccc(CC[C@H]3COC(N)=N3)cc2)cn1]

The title compound was obtained in analogy to example 13 using 5-cyano-2-chloropyrazine instead of bromobenzene in step a). Yellow solid. MS (ISP): 309.1 ([M+H]$^+$).

Example 40

{4-[2-((S)-2-Amino-4,5-dihydro-oxazol-4-yl)-ethyl]-phenyl}-(4-trifluoromethyl-pyrimidin-2-yl)-amine

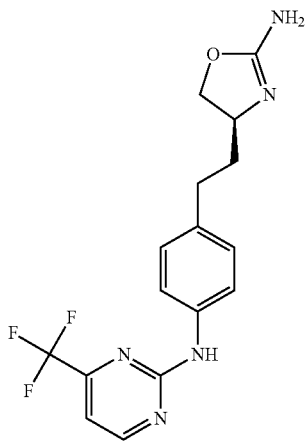 [SMILES: NC1=N[C@@H](CCc2ccc(Nc3nccc(C(F)(F)F)n3)cc2)CO1]

The title compound was obtained in analogy to example 13 using 2-chloro-4-(trifluoromethyl)pyrimidine instead of bromobenzene in step a). Light yellow solid. MS (ISP): 352.1 ([M+H]$^+$).

Example 41

{4-[2-((S)-2-Amino-4,5-dihydro-oxazol-4-yl)-ethyl]-phenyl}-(3-chloro-pyrazin-2-yl)-amine

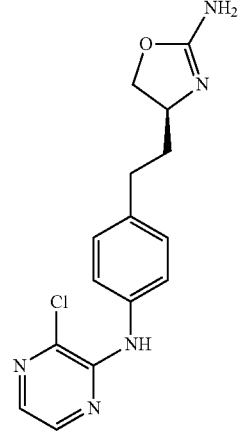 [SMILES: NC1=N[C@@H](CCc2ccc(Nc3nccnc3Cl)cc2)CO1]

The title compound was obtained in analogy to example 13 using 2,3-dichloropyrazine instead of bromobenzene in step a). Yellow solid. MS (ISP): 320.1 ([{$^{37}$Cl}M+H]$^+$), 318.1 ([{$^{35}$Cl}M+H]$^+$).

Example 42

{4-[2-((S)-2-Amino-4,5-dihydro-oxazol-4-yl)-ethyl]-phenyl}-(6-chloro-4-trifluoromethyl-pyridin-2-yl)-amine

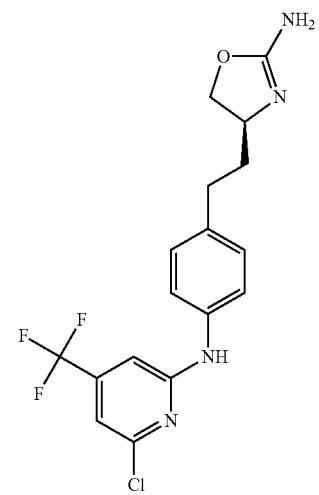 [SMILES: NC1=N[C@@H](CCc2ccc(Nc3cc(C(F)(F)F)cc(Cl)n3)cc2)CO1]

The title compound was obtained in analogy to example 13 using 2,6-dichloro-4-trifluoromethylpyridine instead of bromobenzene in step a). White solid. MS (ISP): 387.1 ([{37Cl}M+H]+), 385.1 ([{35Cl}M+H]+).

Example 43

{4-[2-((S)-2-Amino-4,5-dihydro-oxazol-4-yl)-ethyl]-phenyl}-(6-methyl-pyrazin-2-yl)-amine

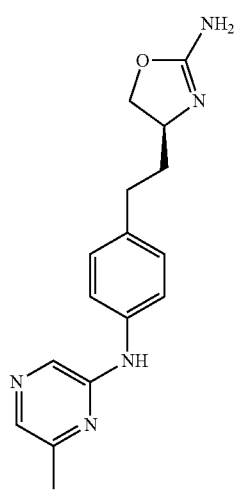 [SMILES: Cc1cncc(Nc2ccc(CC[C@H]3COC(N)=N3)cc2)n1]

The title compound was obtained in analogy to example 13 using 2-chloro-6-methylpyrazine instead of bromobenzene in step a). Light yellow solid. MS (ISP): 298.2 ([M+H]+).

Example 44

{4-[2-((S)-2-Amino-4,5-dihydro-oxazol-4-yl)-ethyl]-phenyl}-(6-chloro-2-methoxy-pyrimidin-4-yl)-amine

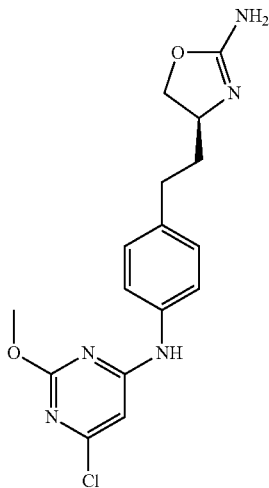 [SMILES: COc1nc(Cl)cc(Nc2ccc(CC[C@H]3COC(N)=N3)cc2)n1]

The title compound was obtained in analogy to example 13 using 4,6-dichloro-2-methoxypyrimidine instead of bromobenzene in step a). White solid. MS (ISP): 350.3 ([{37Cl}M+H]+), 348.2 ([{35Cl}M+H]+).

Example 45

{4-[2-((S)-2-Amino-4,5-dihydro-oxazol-4-yl)-ethyl]-phenyl}-(4-methylsulfanyl-pyrimidin-2-yl)-amine

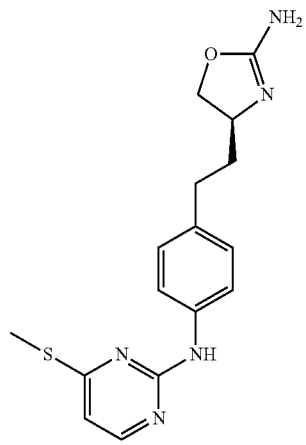 [SMILES: CSc1ccnc(Nc2ccc(CC[C@H]3COC(N)=N3)cc2)n1]

The title compound was obtained in analogy to example 13 using 2-chloro-4-(methylthio)pyrimidine instead of bromobenzene in step a). Amorphous yellow solid. MS (ISP): 330.1 ([M+H]+).

Example 46

{4-[2-((S)-2-Amino-4,5-dihydro-oxazol-4-yl)-ethyl]-phenyl}-(5-methyl-pyrimidin-2-yl)-amine

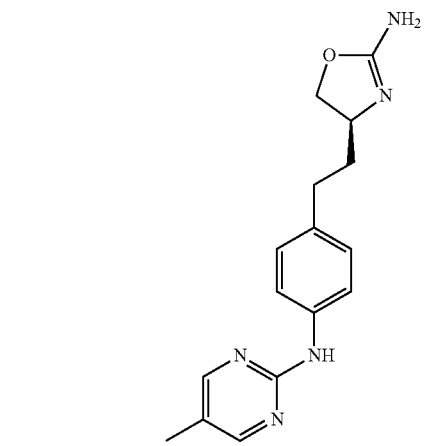 [SMILES: Cc1cnc(Nc2ccc(CC[C@H]3COC(N)=N3)cc2)nc1]

The title compound was obtained in analogy to example 13 using 2-chloro-5-methyl-pyrimidine instead of bromobenzene in step a). White solid. MS (ISP): 298.2 ([M+H]+).

Example 47

1-(2-{4-[2-((S)-2-Amino-4,5-dihydro-oxazol-4-yl)-ethyl]phenylamino}-pyrimidin-5-yl)-ethanone

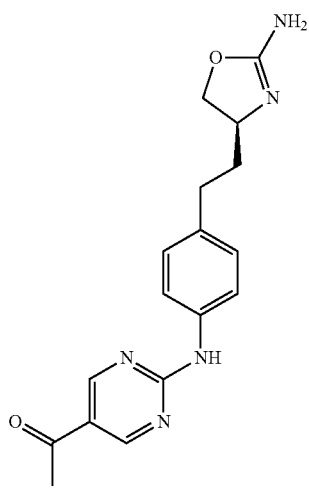 [SMILES: CC(=O)c1cnc(Nc2ccc(CC[C@H]3COC(N)=N3)cc2)nc1]

The title compound was obtained in analogy to example 13 using 1-(2-chloro-pyrimidin-5-yl)-ethanone instead of bromobenzene in step a). White solid. MS (ISP): 326.2 ([M+H]+).

Example 48

{4-[2-((S)-2-Amino-4,5-dihydro-oxazol-4-yl)-ethyl]-phenyl}-(4-methyl-pyrimidin-2-yl)-amine

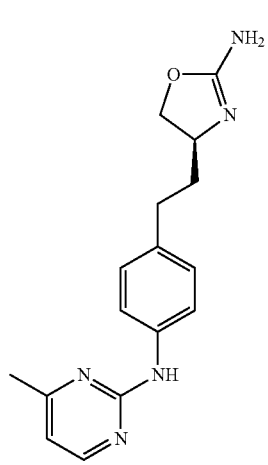 [SMILES: Cc1ccnc(Nc2ccc(CC[C@H]3COC(N)=N3)cc2)n1]

The title compound was obtained in analogy to example 13 using 2-chloro-4-methyl-pyrimidine instead of bromobenzene in step a). Amorphous colourless solid. MS (ISP): 298.2 ([M+H]+).

Example 49

{4-[2-((S)-2-Amino-4,5-dihydro-oxazol-4-yl)-ethyl]-phenyl}-(5-propyl-pyrimidin-2-yl)-amine

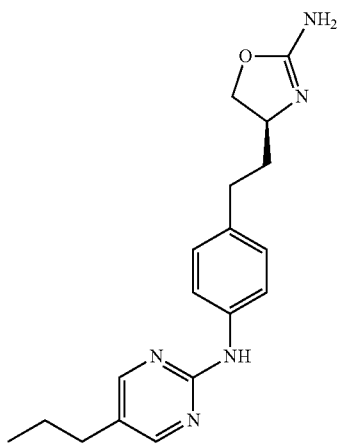 [SMILES: CCCc1cnc(Nc2ccc(CC[C@H]3COC(N)=N3)cc2)nc1]

The title compound was obtained in analogy to example 13 using 2-chloro-5-propylpyrimidine instead of bromobenzene in step a). Light yellow solid. MS (ISP): 326.2 ([M+H]+).

Example 50

{4-[2-((S)-2-Amino-4,5-dihydro-oxazol-4-yl)-ethyl]-phenyl}-(2-chloro-pyrimidin-5-yl)-amine

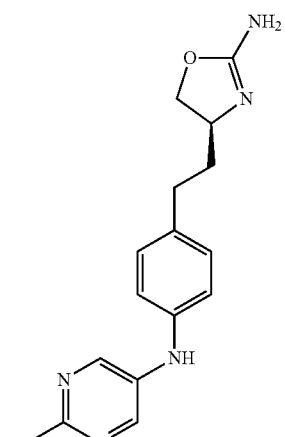

The title compound was obtained in analogy to example 13 using 5-bromo-2-chloropyrimidine instead of bromobenzene in step a). White solid. MS (ISP): 320.1 ([{37Cl}M+H]+), 318.1 ([{35Cl}M+H]+).

Example 51

{4-[2-((S)-2-Amino-4,5-dihydro-oxazol-4-yl)-ethyl]-phenyl}-(5-bromo-pyrimidin-2-yl)-amine

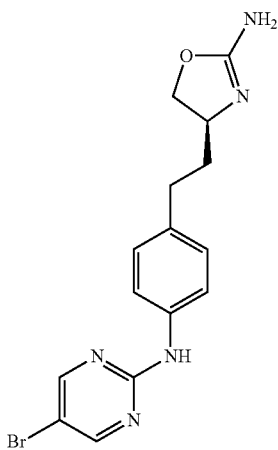

The title compound was obtained in analogy to example 13 using 2,5-dibromopyrimidine instead of bromobenzene in step a). White solid. MS (ISP): 364.1 ([{$^{81}$Br}M+H]$^+$), 362.1 ([{$^{79}$Br}M+H]$^+$).

Example 52

{4-[2-((4S,5S)-2-Amino-5-methyl-4,5-dihydro-oxazol-4-yl)-ethyl]-phenyl}-(5-chloro-pyrimidin-2-yl)-amine

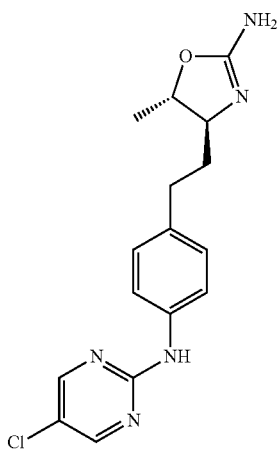 [SMILES: C[C@@H]1OC(N)=N[C@H]1CCc1ccc(Nc2ncc(Cl)cn2)cc1]

a) (S,E)-tert-Butyl 4-(4-bromostyryl)-2,2-dimethyloxazolidine-3-carboxylate

The title compound was obtained in analogy to example 6(a) using (4-bromo-benzyl)-phosphonic acid diethyl ester instead of (4-nitro-benzyl)-phosphonic acid diethyl ester. Yellow solid. MS (ISP): 284.0 ([{$^{81}$Br}M+H–C$_4$H$_8$—CO$_2$]$^+$), 282.0 ([{$^{79}$Br}M+H—C$_4$H$_8$—CO$_2$]$^+$).

b) (E)-(S)-2-Amino-4-(4-bromo-phenyl)-but-3-en-1-ol

To a solution of (S,E)-tert-butyl 4-(4-bromostyryl)-2,2-dimethyloxazolidine-3-carboxylate (13 g) in acetonitrile (30 ml) were added sequentially water (35 ml) and a solution of trifluoroacetic acid (18.3 ml) in water (50 ml). The mixture was heated at 80° C. for 3 hours. The mixture was then cooled to room temperature and diluted with ethyl acetate/THF (1:1). The resulting mixture was washed sequentially with 1 N aq. sodium hydroxide solution and saturated brine, the phases were then separated and the organic phase was dried over sodium sulphate and concentrated in vacuo. The residue was triturated in diethyl ether (40 ml) and the resulting crystals were collected by filtration to afford (E)-(S)-2-amino-4-(4-bromo-phenyl)-but-3-en-1-ol (5.59 g, 68%) as a brown solid. The filtrate was concentrated in vacuo and the residue was purified by column chromatography (SiO$_2$; gradient: 0-30% MeOH in dichloromethane) to afford a further amount of (E)-(S)-2-amino-4-(4-bromo-phenyl)-but-3-en-1-ol (2.21 g, 27%) as a brown solid. MS (ISP): 227.1 ([{$^{81}$Br}M+H—NH$_3$]$^+$), 225.1 ([{$^{79}$Br}M+H—NH$_3$]$^+$).

c) [(E)-(S)-3-(4-Bromo-phenyl)-1-hydroxymethyl-allyl]-carbamic acid tert-butyl ester (E)-(S)-2-amino-4-(4-bromo-phenyl)-but-3-en-1-ol (7.8 g) and N,N-diisopropylethylamine (11.1 ml) were combined with THF (150 ml) to give a colourless solution. The reaction mixture was cooled to 0° C. and di-tert-butyl carbonate (7.17 g) was added. The reaction mixture was stirred at room temperature overnight to afford a yellow solution. The reaction mixture was then poured into EtOAc and washed sequentially with 1 M aq. HCl, 1 M aq. NaOH and saturated brine. The organic layer was dried over Na2SO4, filtered, and the filtrate was then stirred over charcoal (2 g) for 30 min. The mixture was then filtered through celite and the filtrate was concentrated in vacuo to afford [(E)-(S)-3-(4-bromo-phenyl)-1-hydroxymethyl-allyl]-carbamic acid tert-butyl ester as an off-white solid (10.8 g, 98%). MS (ISP): 344.0 ([{$^{81}$Br}M+H]$^+$), 342.0 ([{$^{79}$Br}M+H]$^+$), 287.9 ([{$^{81}$Br}M+H—C$_4$H$_8$]$^+$), 286.0 ([{$^{79}$Br}M+H—C$_4$H$_8$]$^+$).

d) [(S)-3-(4-Bromo-phenyl)-1-hydroxymethyl-propyl]-carbamic acid tert-butyl ester To a solution of [(E)-(S)-3-(4-bromo-phenyl)-1-hydroxymethyl-allyl]-carbamic acid tert-butyl ester (14.7 g) in methanol (150 ml) was added 10% Pt/C (1.68 g) and the resulting mixture was stirred under a H$_2$ balloon at room temperature for 3 hours (whereby the reaction progress was checked continuously by $^1$H NMR). The reaction mixture was filtered through celite and the filtrate was concentrated in vacuo to afford [(S)-3-(4-bromo-phenyl)-1-hydroxymethyl-propyl]-carbamic acid tert-butyl ester as a yellow solid (11.5 g, 78%). MS (ISP): 346.0 ([{$^{81}$Br}M+H]$^+$), 344.0 ([{$^{79}$Br}M+H]$^+$), 289.9 ([{$^{81}$Br}M+H—C$_4$H$_8$]$^+$), 288.0 ([{$^{79}$Br}M+H—C$_4$H$_8$]$^+$), 246.1 ([{$^{81}$Br}M+H—C$_4$H$_8$—CO$_2$]$^+$), 244.1 ([{$^{79}$Br}M+H—C$_4$H$_8$—CO$_2$]$^+$).

e) [(S)-3-(4-Bromo-phenyl)-1-formyl-propyl]-carbamic acid tert-butyl ester

To a solution of [(S)-3-(4-bromo-phenyl)-1-hydroxymethyl-propyl]-carbamic acid tert-butyl ester (11.5 g) and triethylamine (27.9 ml) in DMSO (70 ml) was added dropwise sulfur trioxide-pyridine complex (16.0 g) while the reaction mixture was cooled in a ice bath. The mixture was then stirred at room temperature for 30 min to afford a yellow solution. The reaction mixture was poured into EtOAc and extracted sequentially with water and with saturated brine. The organic layer was dried over Na2SO4 and concentrated in vacuo. The residue was purified by column chromatography (silica gel, heptane/EtOAc 3/1) to afford [(S)-3-(4-bromo-phenyl)-1-formyl-propyl]-carbamic acid tert-butyl ester as a yellow oil (7.3 g, 64%). MS (EI): 343 ([$^{81}$Br]M]$^+$), 341 ([$^{79}$Br]M]$^+$), 287 ([$^{81}$Br]M–C$_4$H$_8$]$^+$), 285 ([$^{79}$Br]M–C$_4$H$_8$]$^+$), 214 ([$^{81}$Br]M–C$_4$H$_8$—CO$_2$]$^+$), 212 ([$^{79}$Br]M–C$_4$H$_8$—CO$_2$]$^+$), 171, 169, 103, 57 ([C$_4$H$_9$]$^+$).

f) {(1S,2RS)-1-[2-(4-Bromo-phenyl)-ethyl]-2-hydroxy-propyl}-carbamic acid tert-butyl ester To a stirred, cooled solution of [(5)-3-(4-bromo-phenyl)-1-formyl-propyl]-carbamic acid tert-butyl ester (7.3 g) in THF (40 ml) and Et2O (30 ml) at 0° C. was added dropwise over 30 min a solution of methylmagnesium bromide (20.0 ml, 3 M solution in Et2O). The reaction mixture was then stirred at room temperature for 4 hours before being quenched by dropwise addition of water (gas formation!). The reaction mixture was then poured into EtOAc, the layers were separated and the organic layer was washed sequentially with diluted aq. HCl (pH 5) and saturated brine, then dried over Na2SO4 and concentrated in vacuo. The residue was purified by flash chromatography (silica gel, gradient: 0% to 80% EtOAc in hexane) to afford {(1S,2RS)-1-[2-(4-bromo-phenyl)-ethyl]-2-hydroxy-propyl}-carbamic acid tert-butyl ester as a colourless amorphous solid comprising a mixture of epimers (5.1 g, 66%). MS (EI): 303 ([$^{81}$Br]M–C$_4$H$_8$]$^+$), 301 ([$^{79}$Br]M–C$_4$H$_8$]$^+$), 258 ([$^{81}$Br]M–C$_4$H$_8$—CO$_2$H]$^+$), 256 ([$^{79}$Br]M–C$_4$H$_8$—CO$_2$H]$^+$), 214, 212, 171, 169, 57 ([C$_4$H$_9$]$^+$).

g) (4S,5S)-4-[2-(4-Bromo-phenyl)-ethyl]-2,2,5-trimethyl-oxazolidine-3-carboxylic acid tert-butyl ester and (4S,5R)-4-[2-(4-Bromo-phenyl)-ethyl]-2,2,5-trimethyl-oxazolidine-3-carboxylic acid tert-butyl ester {(1S,2RS)-1-[2-(4-bromo-phenyl)-ethyl]-2-hydroxy-propyl}-carbamic acid tert-butyl ester (5.07 g), p-toluenesulfonic acid monohydrate (538 mg) and 2,2-dimethoxypropane (26.1 ml) were combined with CH2Cl2 (300 ml) to give a colourless solution. The reaction mixture was stirred at room temperature overnight before being washed with sat. aq. NaHCO3 solution. The layers were separated and the organic layer was dried over Na2SO4 and concentrated in vacuo. The residue was purified by flash chromatography (silica gel, gradient: 0% to 25% EtOAc in hexane) to afford (4S,5S)-4-[2-(4-bromo-phenyl)-ethyl]-2,2,5-trimethyl-oxazolidine-3-carboxylic acid tert-butyl ester as a yellow oil (2.85 g, 51%, fractions eluting first) and (4S,5R)-4-[2-(4-bromo-phenyl)-ethyl]-2,2,5-trimethyl-oxazolidine-3-carboxylic acid tert-butyl ester as a yellow oil (475 mg, 8%, fractions eluting last).

h) (4S,5S)-4-{2-[4-(Benzhydrylidene-amino)-phenyl]-ethyl}-2,2,5-trimethyl-oxazolidine-3-carboxylic acid tert-butyl ester To a solution of (4S,5S)-4-[2-(4-bromo-phenyl)-ethyl]-2,2,5-trimethyl-oxazolidine-3-carboxylic acid tert-butyl ester (3.13 g) in toluene (30 ml) were added diphenylmethanimine (1.71 g) and sodium tert-butoxide (1.06 g). The reaction mixture was degassed by bubbling argon through the mixture for several minutes. BINAP (489 mg) and Pd2(dba)3 (216 mg) were then added and the reaction mixture was stirred at 100° C. for 20 h. The reaction mixture was then cooled to room temperature, poured into EtOAc, and extracted with water. The organic layer was separated, dried over Na2SO4, and concentrated in vacuo. The residue was purified by flash chromatography (silica gel, gradient: 0% to 30% EtOAc in hexane) to afford (4S,5S)-4-{2-[4-(benzhydrylidene-amino)-phenyl]-ethyl}-2,2,5-trimethyl-oxazolidine-3-carboxylic acid tert-butyl ester as a yellow oil (3.2 g, 82%). MS (ISP): 499.3 ([M+H).

i) (4S,5S)-4-[2-(4-Amino-phenyl)-ethyl]-2,2,5-trimethyl-oxazolidine-3-carboxylic acid tert-butyl ester To a solution of (4S,5S)-4-{2-[4-(benzhydrylideneamino)-phenyl]-ethyl}-2,2,5-trimethyl-oxazolidine-3-carboxylic acid tert-butyl ester (3.23 g) in methanol (50 ml) was added ammonium formate (6.13 g). The reaction mixture was degassed by bubbling argon through the mixture for several minutes. 10% Pd/C (207 mg) was added and the reaction mixture was stirred at 60° C. for 1 hour. TLC showed the reaction was complete. The reaction mixture was filtered through celite and concentrated in vacuo. The residue was purified by flash chromatography (silica gel, gradient: 0% to 100% EtOAc in hexane) to afford (4S,5S)-4-[2-(4-amino-phenyl)-ethyl]-2,2,5-trimethyl-oxazolidine-3-carboxylic acid tert-butyl ester as a yellow oil (1.76 g, 81%). MS (ISP): 335.2 ([M+H), 235.2 ([M–C$_4$H$_8$—CO$_2$]$^+$).

j) (4S,5S)-4-{2-[4-(5-Chloro-pyrimidin-2-ylamino)-phenyl]-ethyl}-2,2,5-trimethyl-oxazolidine-3-carboxylic acid tert-butyl ester The title compound was obtained in analogy to example 6(c) using (4S,5S)-4-[2-(4-amino-phenyl)-ethyl]-2,2,5-trimethyl-oxazolidine-3-carboxylic acid tert-butyl ester instead of (S)-4-[2-(4-amino-phenyl)-ethyl]-2,2-dimethyl-oxazolidine-3-carboxylic acid tert-butyl ester and 2,5-dichloropyrimidine instead of 1-bromo-4-chlorobenzene. Yellow oil. MS (ISP): 449.2 ([$^{37}$Cl]M+H]$^+$), 447.2 ([$^{35}$Cl]M+H]$^+$).

k) (2S,3S)-3-Amino-5-[4-(5-chloro-pyrimidin-2-ylamino)-phenyl]-pentan-2-ol

The title compound was obtained in analogy to example 11 step b) using (4S,5S)-4-{2-[4-(5-chloro-pyrimidin-2-ylamino)-phenyl]-ethyl}-2,2,5-trimethyl-oxazolidine-3-carboxylic acid tert-butyl ester in place of (S)-2,2-dimethyl-4-{2-[4-(5-trifluoromethyl-pyridin-2-ylamino)-phenyl]-ethyl}-oxazolidine-3-carboxylic acid tert-butyl ester. White solid. MS (ISP): 309.1 ([$^{37}$Cl]M+H]$^+$), 307.1 ([$^{35}$Cl]M+H]$^+$).

l) {4-[2-((4S,5S)-2-Amino-5-methyl-4,5-dihydro-oxazol-4-yl)-ethyl]-phenyl}-(5-chloro-pyrimidin-2-yl)-amine The title compound was obtained in analogy to example 6 step e) using (2S,3S)-3-amino-5-[4-(5-chloro-pyrimidin-2-ylamino)-phenyl]-pentan-2-ol instead of (S)-2-amino-4-[4-

(4-chloro-phenylamino)-phenyl]-butan-1-ol. White solid. MS (ISP): 334.1 ([{$^{37}$Cl}M+H]$^+$), 332.1 ([{$^{35}$Cl}M+H]$^+$).

Example 53

(S)-1-(2-(4-(2-(2-Amino-4,5-dihydrooxazol-4-yl)ethyl)phenylamino)pyrimidin-5-yl)propan-1-one

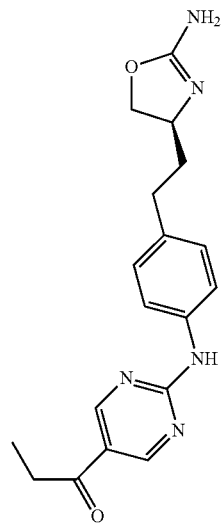 [SMILES: CCC(=O)c1cnc(Nc2ccc(CC[C@H]3COC(N)=N3)cc2)nc1]

The title compound was obtained in analogy to example 13 using 1-(2-chloropyrimidin-5-yl)propan-1-one (CAS 212621-61-9) instead of bromobenzene in step a). Yellow solid. MS (ISP): 340.3 ([M+H]$^+$).

Example 54

{4-[2-((S)-2-Amino-4,5-dihydro-oxazol-4-yl)-ethyl]-phenyl}-(5-cyclopropyl-pyrimidin-2-yl)-amine

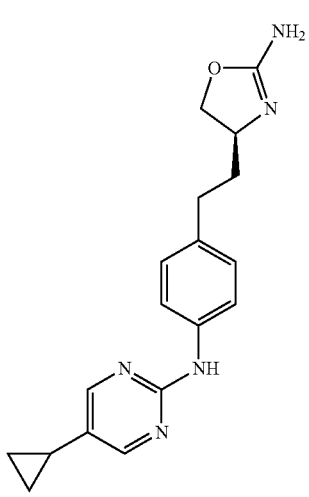 [SMILES: NC1=N[C@@H](CCc2ccc(Nc3ncc(C4CC4)cn3)cc2)CO1]

The title compound was obtained in analogy to example 13 using 2-chloro-5-cyclopropylpyrimidine (CAS 166740-44-9) instead of bromobenzene in step a). Off-white solid. MS (ISP): 324.3 ([M+H]$^+$).

Example 55

{4-[2-((S)-2-Amino-4,5-dihydro-oxazol-4-yl)-ethyl]-phenyl}-(5-ethoxy-pyrimidin-2-yl)-amine

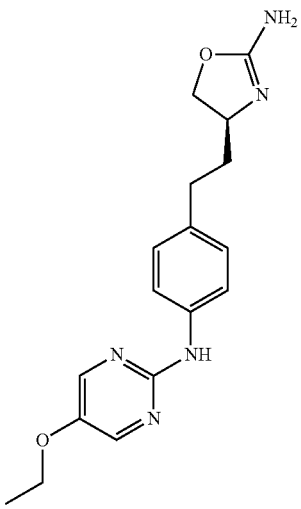 [SMILES: CCOc1cnc(Nc2ccc(CC[C@H]3COC(N)=N3)cc2)nc1]

The title compound was obtained in analogy to example 13 using 2-chloro-5-ethoxypyrimidine instead of bromobenzene in step a). White solid. MS (ISP): 328.3 ([M+H]$^+$).

Example 56

(S)-4-(4-(5-(Trifluoromethyl)pyrimidin-2-ylamino)phenethyl)-4,5-dihydrooxazol-2-amine

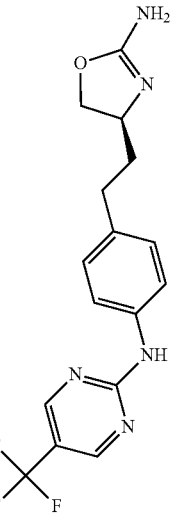

a) Trifluoro-methanesulfonic acid 5-trifluoromethyl-pyrimidin-2-yl ester

To a solution of 5-(trifluoromethyl)pyrimidin-2-ol (300 mg) in dichloromethane (10 ml) at 0° C. were added dropwise N,N-diisopropylethylamine (939 µl) and trifluoromethanesulfonic anhydride (185 µl). The reaction mixture was stirred at 0° C. for 2 h. The crude reaction mixture was then concentrated in vacuo to afford a red solid contained trifluoro-methanesulfonic acid 5-trifluoromethyl-pyrimidin-2-yl ester which was used immediately in the next step without further purification.

b) (S)-4-(4-(5-(Trifluoromethyl)pyrimidin-2-ylamino)phenethyl)-4,5-dihydrooxazol-2-amine The title compound was obtained in analogy to example 13 using trifluoro-methanesulfonic acid 5-trifluoromethyl-pyrimidin-2-yl ester instead of bromobenzene in step a). Yellow solid. MS (ISP): 352.3 ([M+H]$^+$).

Example 57

(S)-4-(4-(5-tert-Butylpyrimidin-2-ylamino)phenethyl)-4,5-dihydrooxazol-2-amine

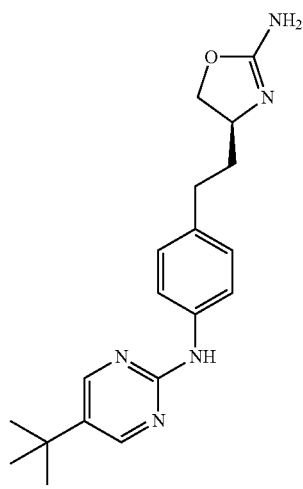 [SMILES: CC(C)(C)c1cnc(Nc2ccc(CC[C@H]3COC(N)=N3)cc2)nc1]

a) (S)-tert-Butyl 4-(4-(5-bromopyrimidin-2-ylamino)phenethyl)-2,2-dimethyloxazolidine-3-carboxylate The title compound was obtained in analogy to example 6 steps a)-c) using 2,5-dibromopyrimidine instead of 1-bromo-4-chlorobenzene in step c). Yellow oil. MS (ISP): 479.1 ([{$^{81}$Br}M+H]$^+$), 477.1 ([{$^{79}$Br}M+H]$^+$).

b) (S)-tert-Butyl 4-(4-(5-tert-butylpyrimidin-2-ylamino)phenethyl)-2,2-dimethyloxazolidine-3-carboxylate To (S)-tert-butyl 4-(4-(5-bromopyrimidin-2-ylamino) phenethyl)-2,2-dimethyloxazolidine-3-carboxylate (100 mg) and bis(tri-t-butylphosphine)palladium(0) (21.4 mg) in THF (10 ml) under argon was added tert-butylzinc(II) bromide (1.26 ml, 0.5 M solution in THF). The reaction mixture was stirred at 22° C. for 1 hour. The reaction was quenched by addition of EtOAc then washed sequentially with saturated aqueous ammonium chloride solution and 1 N aqueous sodium bicarbonate solution. The phases were separated and the organic phase was dried over MgSO4, filtered and then concentrated in vacuo. The crude material was purified by preparative HPLC (Column: Zorbax 5 micron C18 50×20, flow rate: 30 ml/min; eluant gradient: water (+0.1% formic acid)/acetonitrile (80%-20% to 5%-95%)) to afford (S)-tert-butyl 4-(4-(5-tert-butylpyrimidin-2-ylamino)phenethyl)-2,2-dimethyloxazolidine-3-carboxylate (8.4 mg, 9%) as a yellow oil. MS (ISP): 455.5 ([M+H]$^+$).

c) (S)-2-Amino-4-(4-(5-tert-butylpyrimidin-2-ylamino)phenyl)butan-1-ol

The title compound was obtained in analogy to example 11 step b) using (S)-tert-butyl 4-(4-(5-tert-butylpyrimidin-2-ylamino)phenethyl)-2,2-dimethyloxazolidine-3-carboxylate in place of (S)-2,2-dimethyl-4-{2-[4-(5-trifluoromethyl-pyridin-2-ylamino)-phenyl]-ethyl}-oxazolidine-3-carboxylic acid tert-butyl ester. Amorphous solid. MS (ISP): 315.3 ([M+H]$^+$).

d) (S)-4-(4-(5-tert-Butylpyrimidin-2-ylamino)phenethyl)-4,5-dihydrooxazol-2-amine The title compound was obtained in analogy to example 6 step e) using (S)-2-amino-4-(4-(5-tert-butylpyrimidin-2-ylamino)phenyl)butan-1-ol instead of (S)-2-amino-4-[4-(4-chloro-phenylamino)-phenyl]-butan-1-ol. White solid. MS (ISP): 340.4 ([M+H]$^+$).

Example 58

(S)-4-(4-(5-(Pentan-3-yl)pyrimidin-2-ylamino)phenethyl)-4,5-dihydrooxazol-2-amine

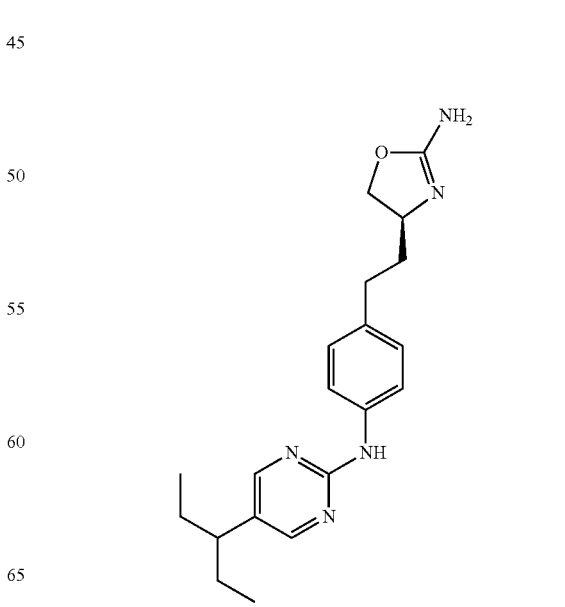

The title compound was obtained in analogy to example 57 using pentan-3-ylzinc(II) bromide instead of tert-butylzinc (II) bromide in step b). White solid. MS (ISP): 354.3 ([M+H]+).

Example 59

2-{4-[2-((S)-2-Amino-4,5-dihydro-oxazol-4-yl)-ethyl]-phenylamino}-pyrimidine-5-carbonitrile

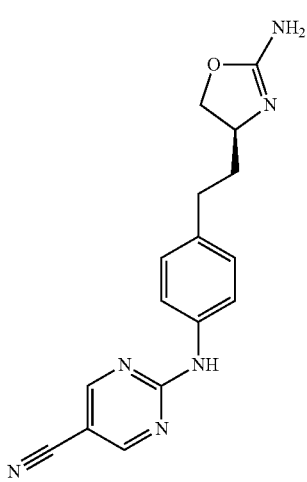

The title compound was obtained in analogy to example 13 using 2-chloropyrimidine-5-carbonitrile instead of bromobenzene in step a). White solid. MS (ISP): 309.2 ([M+H]+).

Example 60

(S)-4-(4-(5-Cyclobutylpyrimidin-2-ylamino)phenethyl)-4,5-dihydrooxazol-2-amine

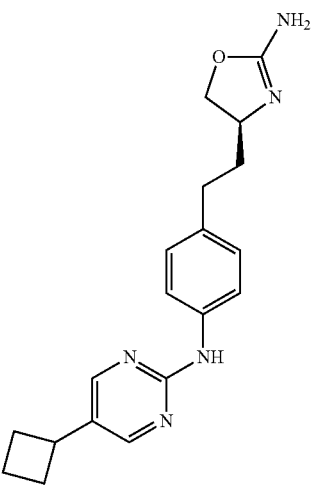 [SMILES: NC1=N[C@@H](CCc2ccc(Nc3ncc(C4CCC4)cn3)cc2)CO1]

The title compound was obtained in analogy to example 57 using cyclobutylzinc(II) bromide instead of tert-butylzinc(II) bromide in step b). White solid. MS (ISP): 338.3 ([M+H]+).

Example 61

(S)-4-(4-(5-Isopropylpyrimidin-2-ylamino)phenethyl)-4,5-dihydrooxazol-2-amine

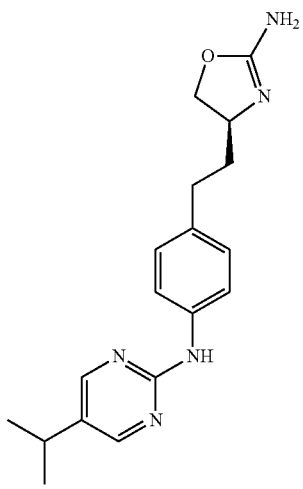 [SMILES: CC(C)c1cnc(Nc2ccc(CC[C@H]3COC(N)=N3)cc2)nc1]

The title compound was obtained in analogy to example 57 using isopropylzinc(II) bromide instead of tert-butylzinc(II) bromide in step b). White solid. MS (ISP): 326.3 ([M+H]+).

Example 62

(S)-4-(2-{4-[1-(5-Bromo-pyridin-2-yl)-2,2,2-trifluoro-ethylamino]-phenyl}-ethyl)-4,5-dihydro-oxazol-2-ylamine

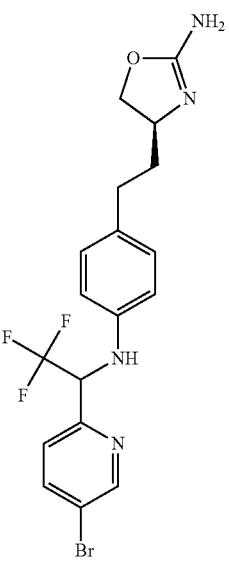 [SMILES: NC1=N[C@@H](CCc2ccc(NC(c3ccc(Br)cn3)C(F)(F)F)cc2)CO1]

a) (RS)-1-(5-Bromo-pyridin-2-yl)-2,2,2-trifluoro-ethanol

To a cooled, stirred solution of 5-bromopyridine-2-carbaldehyde (3.72 g, CAS 31181-90-5) and (trifluoromethyl)trimethylsilane (3.56 ml) in THF (30 ml) at 0° C. was added dropwise tetrabutylammonium fluoride solution (1.0 ml, 1 M solution in THF). The reaction mixture was stirred at 0° C. for 30 min and then at room temperature for 2 hours. The mixture was then diluted with 1 N aq. HCl (20 ml) and stirring was continued for a further 2 hours. The mixture was diluted with water and extracted twice with ethyl acetate. The combined organic phases were dried over sodium sulfate and concentrated in vacuo. The residue was purified by column chromatography (SiO$_2$; gradient: heptane/EtOAc) to give (RS)-1-(5-bromo-pyridin-2-yl)-2,2,2-trifluoro-ethanol as a light yellow solid (3.35 g, 65%). MS (ISP): 258.0 ([{$^{81}$Br}M+H]$^+$), 256.1 ([{$^{79}$Br}M+H]$^+$).

b) (RS)-Trifluoro-methanesulfonic acid 1-(5-bromo-pyridin-2-yl)-2,2,2-trifluoro-ethyl ester To a stirred suspension of sodium hydride (765 mg, 60% dispersion in mineral oil) in dry diethyl ether (20 ml) under an argon atmosphere at 0° C. was added dropwise a solution of (RS)-1-(5-bromo-pyridin-2-yl)-2,2,2-trifluoro-ethanol (3.06 g) in diethyl ether (10 ml) and the resulting mixture was stirred at room temperature for 30 min. Trifluoromethanesulfonyl chloride (1.4 ml) was added and stirring was continued for a further 15 min at room temperature. The reaction mixture was quenched by addition of 10% aq. sodium bicarbonate solution and the mixture was extracted with diethyl ether. The phases were separated and the organic phase was washed with saturated brine. The organic phase was separated, dried over sodium sulphate, and concentrated in vacuo. The reside was purified by Kugelrohr distillation (60° C. oven temperature, 0.3 mbar) to give (RS)-trifluoro-methanesulfonic acid 1-(5-bromo-pyridin-2-yl)-2,2,2-trifluoro-ethyl ester (3.6 g, 78%) as a white solid. MS (EI): 389 ([{$^{81}$Br}M]$^+$), 387 ([{$^{79}$Br}M]$^+$), 320 ([{$^{81}$Br}M–CF$_3$]$^+$), 318 ([{$^{79}$Br}M–CF$_3$]$^+$), 256 ([{$^{81}$Br}M–CF$_3$—SO$_2$]$^+$), 254 ([{$^{79}$Br}M–CF$_3$—SO$_2$]$^+$), 240 ([{$^{81}$Br}M–OSO$_2$CF$_3$]$^+$), 238 ([{$^{79}$Br}M–OSO$_2$CF$_3$]$^+$).

c) (S)-4-(2-{4-[1-(5-Bromo-pyridin-2-yl)-2,2,2-trifluoro-ethylamino]-phenyl}-ethyl)-2,2-dimethyl-oxazolidine-3-carboxylic acid tert-butyl ester To a stirred solution of (S)-4-[2-(4-amino-phenyl)-ethyl]-2,2-dimethyl-oxazolidine-3-carboxylic acid tert-butyl ester (150 mg, example 6b) in dry THF (0.2 ml) under an argon atmosphere was added sodium hydride (34 mg, 60% dispersion in mineral oil) and stirring was continued for 15 minutes. Trifluoro-methanesulfonic acid 1-(5-bromo-pyridin-2-yl)-2,2,2-trifluoro-ethyl ester (182 mg) was then added and the mixture was stirred overnight at room temperature. The reaction mixture was diluted with ethyl acetate and washed sequentially with water and with saturated brine. The organic phase was separated, dried over sodium sulphate, and concentrated in vacuo. The reside was purified by column chromatography (SiO$_2$; gradient: heptane/EtOAc) to give (S)-4-(2-{4-[1-(5-bromo-pyridin-2-yl)-2,2,2-trifluoro-ethylamino]-phenyl}-ethyl)-2,2-dimethyl-oxazolidine-3-carboxylic acid tert-butyl ester (99 mg, 38%) as a yellow oil. MS (ISP): 560.1 ([{$^{81}$Br}M+H]$^+$), 558.1 ([{$^{79}$Br}M+H]$^+$).

d) (S)-2-Amino-4-{4-[1-(5-bromo-pyridin-2-yl)-2,2,2-trifluoro-ethylamino]-phenyl}-butan-1-ol The title compound was obtained in analogy to example 11 step b) using (S)-4-(2-{4-[1-(5-bromo-pyridin-2-yl)-2,2,2-trifluoro-ethylamino]-phenyl}-ethyl)-2,2-dimethyl-oxazolidine-3-carboxylic acid tert-butyl ester in place of (S)-2,2-dimethyl-4-{2-[4-(5-trifluoromethyl-pyridin-2-ylamino)-phenyl]-ethyl}-oxazolidine-3-carboxylic acid tert-butyl ester. Yellow oil. MS (ISP): 420.1 ([{$^{81}$Br}M+H]$^+$), 418.2 ([{$^{79}$Br}M+H]$^+$).

e) (S)-4-(2-{4-[1-(5-Bromo-pyridin-2-yl)-2,2,2-trifluoro-ethylamino]-phenyl}-ethyl)-4,5-dihydro-oxazol-2-ylamine The title compound was obtained in analogy to example 6 step e) using (S)-2-amino-4-{4-[1-(5-bromo-pyridin-2-yl)-2,2,2-trifluoro-ethylamino]-phenyl}-butan-1-ol instead of (S)-2-amino-4-[4-(4-chloro-phenylamino)-phenyl]-butan-1-ol. Amorphous yellow solid. MS (ISP): 445.1 ([{$^{81}$Br}M+H]$^+$), 443.1 ([{$^{79}$Br}M+H]$^+$).

Example 63

(4S)-4-(4-(1-(4-Chlorophenyl)-2,2,2-trifluoroethylamino)phenethyl)-4,5-dihydrooxazol-2-amine (1:1 mixture of epimers)

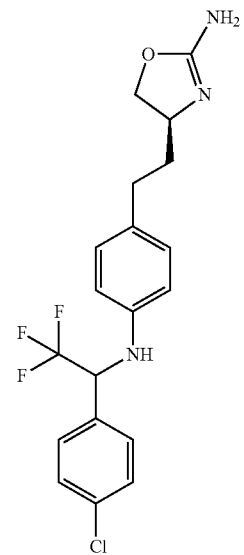 [SMILES: NC1=N[C@@H](CCc2ccc(NC(c3ccc(Cl)cc3)C(F)(F)F)cc2)CO1]

The title compound was obtained in analogy to example 62 using 4-chloro-benzaldehyde instead of 5-bromopyridine-2-carbaldehyde 1 in step a). Colourless foam. MS (ISP): 400.2 ([{$^{37}$Cl}M+H]$^+$), 398.2 ([{$^{35}$Cl}M+H]$^+$).

Examples 64 & 65

(+)-(S)-4-(4-((S)-1-(4-Chlorophenyl)-2,2,2-trifluoro-ethylamino)phenethyl)-4,5-dihydrooxazol-2-amine & (−)-(S)-4-(4-((R)-1-(4-chlorophenyl)-2,2,2-trifluoroethylamino)phenethyl)-4,5-dihydrooxazol-2-amine

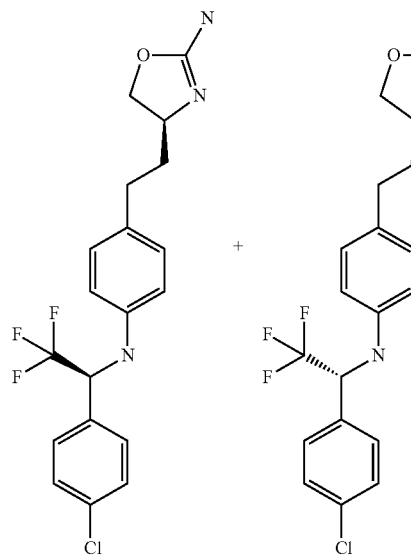

(4S)-4-(4-(1-(4-Chlorophenyl)-2,2,2-trifluoroethylamino)phenethyl)-4,5-dihydrooxazol-2-amine (1:1 mixture of epimers) was separated by preparative chiral HPLC (Chiralpak AD, eluant: heptane/EtOH 6/4). 1$^{st}$ fraction: (+)-(S)-4-(4-((S)-1-(4-chlorophenyl)-2,2,2-trifluoroethylamino) phenethyl)-4,5-dihydrooxazol-2-amine Colourless oil. MS (ISP): 400.2 ([{$^{37}$Cl}M+H]$^+$), 398.2 ([{$^{35}$Cl}M+H]$^+$). 2$^{nd}$ fraction: (−)-(S)-4-(4-((R)-1-(4-chlorophenyl)-2,2,2-trifluoroethylamino)phenethyl)-4,5-dihydrooxazol-2-amine Colourless oil. MS (ISP): 400.2 ([{$^{37}$Cl}M+H]$^+$), 398.2 ([{$^{35}$Cl}M+H]$^+$).

Example 66

(4S)-4-(4-(2,2,2-Trifluoro-1-(3-fluorophenyl)ethylamino)phenethyl)-4,5-dihydrooxazol-2-amine

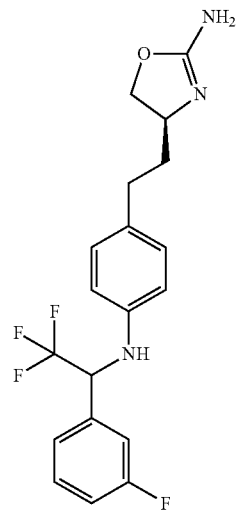 [SMILES: NC1=N[C@@H](CCc2ccc(NC(c3cccc(F)c3)C(F)(F)F)cc2)CO1]

The title compound was obtained in analogy to example 62 using 3-fluoro-benzaldehyde instead of 5-bromopyridine-2-carbaldehyde in step a). Colourless oil. MS (ISP): 382.2 ([M+H]$^+$).

Example 67

(4S)-4-(4-(2,2,2-Trifluoro-1-(4-(trifluoromethyl) phenyl)ethylamino)phenethyl)-4,5-dihydrooxazol-2-amine

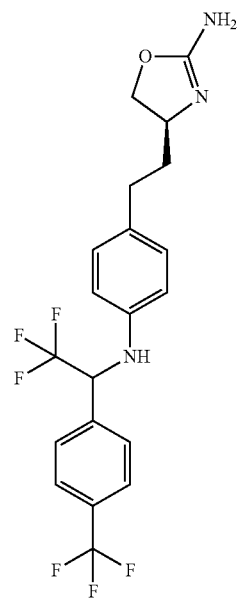 [SMILES: NC1=N[C@@H](CCc2ccc(NC(c3ccc(C(F)(F)F)cc3)C(F)(F)F)cc2)CO1]

The title compound was obtained in analogy to example 62 using 4-trifluoromethyl-benzaldehyde instead of 5-bromopyridine-2-carbaldehyde in step a). Colourless oil. MS (ISP): 432.2 ([M+H]$^+$).

Example 68

(4S)-4-(4-(1-(5-Chloropyridin-2-yl)-2,2,2-trifluoro-ethylamino)phenethyl)-4,5-dihydrooxazol-2-amine

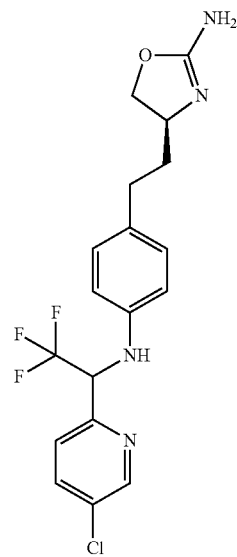 [SMILES: NC1=N[C@@H](CCc2ccc(NC(c3ccc(Cl)cn3)C(F)(F)F)cc2)CO1]

The title compound was obtained in analogy to example 62 using 5-chloropyridine-2-carbaldehyde instead of 5-bromopyridine-2-carbaldehyde in step a). Light yellow oil. MS (ISP): 401.2 ([{$^{37}$Cl}M+H]$^+$), 399.2 ([{$^{35}$Cl}M+H]$^+$).

Example 69

(4S)-4-(4-(1-(3,5-Dichlorophenyl)-2,2,2-trifluoroethylamino)phenethyl)-4,5-dihydrooxazol-2-amine

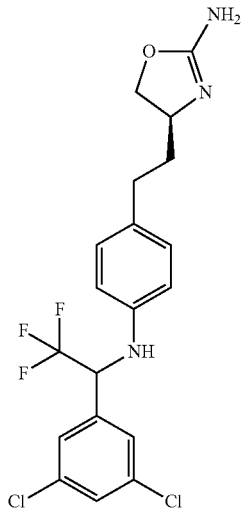 [SMILES: NC1=N[C@@H](CCc2ccc(NC(c3cc(Cl)cc(Cl)c3)C(F)(F)F)cc2)CO1]

The title compound was obtained in analogy to example 62 using 3,5-dichloro-benzaldehyde instead of 5-bromopyridine-2-carbaldehyde in step a). Colourless waxy solid. MS (ISP): 436.2 ([{$^{37}$Cl}M+H]$^+$), 434.2 ([{$^{37}$Cl$^{35}$Cl}M+H]$^+$), 432.2 ([{$^{35}$Cl}M+H]$^+$).

Example 70

(4S)-4-(4-(2,2,2-Trifluoro-1-(6-methoxypyridin-2-yl)ethylamino)phenethyl)-4,5-dihydrooxazol-2-amine

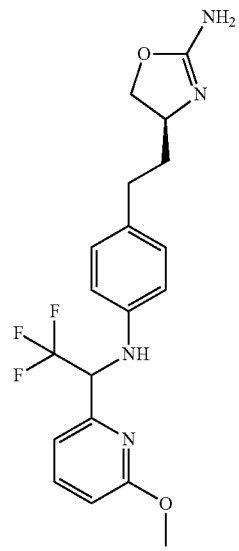 [SMILES: COc1cccc(C(Nc2ccc(CC[C@H]3COC(N)=N3)cc2)C(F)(F)F)n1]

The title compound was obtained in analogy to example 62 using 6-methoxypyridine-2-carbaldehyde instead of 5-bromopyridine-2-carbaldehyde in step a). Colourless oil. MS (ISP): 395.2 ([M+H]$^+$).

Example 71

{5-[2-((S)-2-Amino-4,5-dihydro-oxazol-4-yl)-ethyl]-pyridin-2-yl}-(5-chloro-pyrimidin-2-yl)-amine

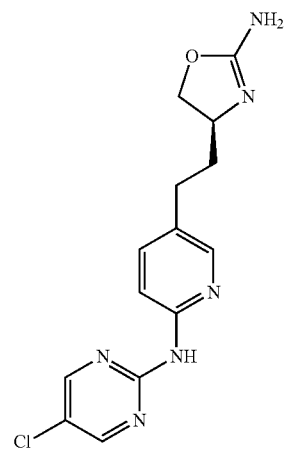 [SMILES: NC1=N[C@@H](CCc2ccc(Nc3ncc(Cl)cn3)nc2)CO1]

a) (S)-4-[(E)-2-(6-Chloro-pyridin-3-yl)-vinyl]-2,2-dimethyl-oxazolidine-3-carboxylic acid tert-butyl ester The title compound was obtained in analogy to example 6 step (a) using (6-chloro-pyridin-3-ylmethyl)-phosphonic acid diethyl ester (CAS 561066-65-7) instead of (4-nitrobenzyl)-phosphonic acid diethyl ester. Yellow oil. MS (ISP): 341.2 ([{$^{37}$Cl}M+H]$^+$), 339.1 ([{35Cl}M+H]$^+$).

b) (S)-4-[2-(6-Chloro-pyridin-3-yl)-ethyl]-2,2-dimethyl-oxazolidine-3-carboxylic acid tert-butyl ester To a stirred suspension of (S)-4-[(E)-2-(6-chloro-pyridin-3-yl)-vinyl]-2,2-dimethyl-oxazolidine-3-carboxylic acid tert-butyl ester (1.0 g) in methanol (70 ml) was added platinum on charcoal (0.58 g, 10 wt %) and the mixture was stirred under an atmosphere of hydrogen at room temperature for 15 min. The mixture was then filtered through celite and the filtrate was concentrated in vacuo to give (S)-4-[2-(6-chloro-pyridin-3-yl)-ethyl]-2,2-dimethyl-oxazolidine-3-carboxylic acid tert-butyl ester (949 mg, 94%) as a colourless oil. MS (ISP): 343.2 ([{$^{37}$Cl}M+H]$^+$), 341.1 ([{$^{35}$Cl}M+H]$^+$), 287.0 ([{$^{37}$Cl}M+H—C$_4$H$_8$]$^+$), 285.1 ([{$^{35}$Cl}M+H—C$_4$H$_8$]$^+$).

c) (S)-4-{2-[6-(5-Chloro-pyrimidin-2-ylamino)-pyridin-3-yl]-ethyl}-2,2-dimethyl-oxazolidine-3-carboxylic acid tert-butyl ester In a pressure tube, (S)-4-[2-(6-chloro-pyridin-3-yl)-ethyl]-2,2-dimethyl-oxazolidine-3-carboxylic acid tert-butyl ester (0.94 g), 5-chloropyrimidin-2-amine (357 mg) and cesium carbonate (1.35 g) were combined with dioxane (5 ml) to give a yellow suspension. The mixture was degassed by bubbling through argon for several minutes. Xantphos (96 mg) and tris(dibenzylideneacetone)dipalladium chloroform complex (86 mg) were then added and the tube was sealed. The reaction mixture was stirred at 100° C. overnight. The reaction mixture was then cooled to room temperature and concentrated in vacuo. The residue was purified by flash chromatography (SiO$_2$; gradient: 0% to 70% EtOAc in hexane) to afford (S)-4-{2-[6-(5-chloro-pyrimidin-2-ylamino)-pyridin-3-yl]-ethyl}-2,2-dimethyl-oxazolidine-3-carboxylic acid tert-butyl ester (417 mg, 35%) as a yellow solid. MS (ISP): 436.3 ([{$^{37}$Cl}M+H]$^+$), 434.4 ([{$^{35}$Cl}M+H]$^+$), 380.3 ([{$^{37}$Cl}M+H—C$_4$H$_8$]$^+$), 378.3 ([{$^{35}$Cl}M+H—C$_4$H$_8$]$^+$).

d) (S)-2-Amino-4-[6-(5-chloro-pyrimidin-2-ylamino)-pyridin-3-yl]-butan-1-ol

The title compound was obtained in analogy to example 11 step b) using (S)-4-{2-[6-(5-chloro-pyrimidin-2-ylamino)-pyridin-3-yl]-ethyl}-2,2-dimethyl-oxazolidine-3-carboxylic acid tert-butyl ester in place of (S)-2,2-dimethyl-4-{2-[4-(5-trifluoromethyl-pyridin-2-ylamino)-phenyl]-ethyl}-oxazolidine-3-carboxylic acid tert-butyl ester. Light brown solid. MS (ISP): 296.3 ([{$^{37}$Cl}M+H]$^+$), 294.1 ([{$^{35}$Cl}M+H]$^+$).

e) {5-[2-((S)-2-Amino-4,5-dihydro-oxazol-4-yl)-ethyl]-pyridin-2-yl}-(5-chloro-pyrimidin-2-yl)-amine The title compound was obtained in analogy to example 6 step e) using (S)-2-amino-4-[6-(5-chloro-pyrimidin-2-ylamino)-pyridin-3-yl]-butan-1-ol instead of (S)-2-amino-4-[4-(4-chloro-phenylamino)-phenyl]-butan-1-ol. White solid. MS (ISP): 321.1 ([{$^{37}$Cl}M+H]$^+$), 319.1 ([{$^{35}$Cl}M+H]$^+$).

Example 72

{4-[2-((S)-2-Amino-4,5-dihydro-oxazol-4-yl)-ethyl]-2-methyl-phenyl}-(5-chloro-pyrimidin-2-yl)-amine

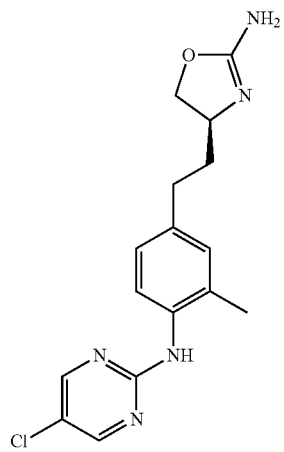 [SMILES: Cc1cc(CC[C@H]2COC(N)=N2)ccc1Nc1ncc(Cl)cn1]

a) (S)-4-{2-[4-(5-Chloro-pyrimidin-2-ylamino)-3-methyl-phenyl]-ethyl}-2,2-dimethyl-oxazolidine-3-carboxylic acid tert-butyl ester The title compound was obtained in analogy to example 6 steps a)-c) using (3-methyl-4-nitrobenzyl)-phosphonic acid diethyl ester (CAS 873458-20-9) instead of (4-nitro-benzyl)-phosphonic acid diethyl ester in step a) and 2,5-dichloropyrimidine instead of 1-bromo-4-chlorobenzene in step c). Yellow oil. MS (ISP): 449.0 ([{$^{37}$Cl}M+H]$^+$), 447.3 ([{$^{35}$Cl}M+H]$^+$), 393.3 ([{$^{37}$Cl}M+H—C$_4$H$_8$]$^+$), 391.1 ([{$^{35}$Cl}M+H—C$_4$H$_8$]$^+$).

b) (S)-2-Amino-4-[4-(5-chloro-pyrimidin-2-ylamino)-3-methyl-phenyl]-butan-1-ol The title compound was obtained in analogy to example 11 step b) using (S)-4-{2-[4-(5-chloro-pyrimidin-2-ylamino)-3-methyl-phenyl]-ethyl}-2,2-dimethyl-oxazolidine-3-carboxylic acid tert-butyl ester in place of (S)-2,2-dimethyl-4-{2-[4-(5-trifluoromethyl-pyridin-2-ylamino)-phenyl]-ethyl}-oxazolidine-3-carboxylic acid tert-butyl ester. White solid. MS (ISP): 309.2 ([{$^{37}$Cl}M+H]$^+$), 307.3 ([{$^{35}$Cl}M+H]$^+$).

c) {4-[2-((S)-2-Amino-4,5-dihydro-oxazol-4-yl)-ethyl]-2-methyl-phenyl}-5-chloro-pyrimidin-2-yl)-amine The title compound was obtained in analogy to example 6 step e) using (S)-2-amino-4-[4-(5-chloro-pyrimidin-2-ylamino)-3-methyl-phenyl]-butan-1-ol instead of (S)-2-amino-4-[4-(4-chloro-phenylamino)-phenyl]-butan-1-ol. Off-white solid. MS (ISP): 334.1 ([{$^{37}$Cl}M+H]$^+$), 332.1 ([{$^{35}$Cl}M+H]$^+$).

Example 73

(S)-4-(4-(5-(2,2,2-Trifluoroethoxy)pyrimidin-2-ylamino)phenethyl)-4,5-dihydrooxazol-2-amine

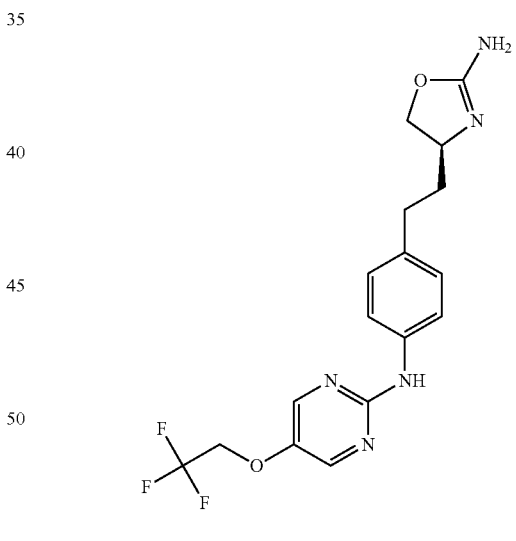

a) 5-Bromo-2-(2,2,2-trifluoro-ethoxy)-pyrimidine

To sodium hydride (303 mg) under an argon atmosphere at 0° C. was added dropwise 2,2,2-trifluoroethanol (775 µl) and the mixture was then stirred at RT for 90 min. A solution of 2,5-dibromopyrimidine (1.5 g) in DMF (8 ml) was then added and stirring continued at RT for 2 hours. The reaction mixture was poured into ice (50 mL) and extracted with EtOAc (2×50 mL). The organic layers were dried over MgSO$_4$ and concentrated in vacuo to afford 5-bromo-2-(2,2,2-trifluoro-ethoxy)-pyrimidine (790 mg, 49%) as a yellow oil which was used in the next step without further purification. MS (EI): 258 ([{$^{81}$Br}M]$^+$), 256 ([{$^{79}$Br}M]$^+$), 189 ([{$^{81}$Br}M–CF$_3$]$^+$), 187 ([{79Br}M–CF$_3$]$^+$).

b) (S)-4-(4-(5-(2,2,2-Trifluoroethoxy)pyrimidin-2-ylamino)phenethyl)-4,5-dihydrooxazol-2-amine The title compound was obtained in analogy to example 13 using 5-bromo-2-(2,2,2-trifluoro-ethoxy)-pyrimidine instead of bromobenzene in step a). Yellow oil. MS (ISP): 382.2 ([M+H]$^+$).

Example 74

(S)-4-(4-(5-(Methylsulfonyl)pyrimidin-2-ylamino)phenethyl)-4,5-dihydrooxazol-2-amine

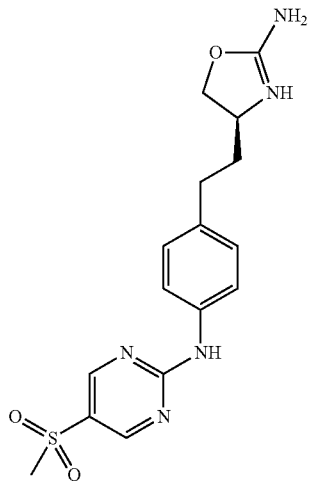 [SMILES: CS(=O)(=O)c1cnc(Nc2ccc(CC[C@H]3COC(N)=N3)cc2)nc1]

a) (5)-tert-Butyl 2,2-dimethyl-4-(4-(5-(methylthio)pyrimidin-2-ylamino)phenethyl)oxazolidine-3-carboxylate The title compound was obtained in analogy to example 6 steps a)-c) using 2-chloro-5-(methylthio)pyrimidine (CAS 115581-36-7) instead of 1-bromo-4-chlorobenzene in step c). Yellow oil. MS (ISP): 445.2 ([M+H]$^+$).

b) (4S)-tert-Butyl 2,2-dimethyl-4-(4-(5-(methylsulfinyl)pyrimidin-2-ylamino)phenethyl)oxazolidine-3-carboxylate To a stirred solution of (5)-tert-butyl 2,2-dimethyl-4-(4-(5-(methylthio)pyrimidin-2-ylamino)phenethyl)oxazolidine-3-carboxylate (393 mg) in dichloromethane (5 ml) was added m-CPBA (218 mg) and stirring was continued at RT for 40 min. The reaction mixture was then diluted with aq. Na$_2$SO$_3$ solution and extracted with dichloromethane. The organic layers were dried over MgSO$_4$ and concentrated in vacuo to give (4S)-tert-butyl 2,2-dimethyl-4-(4-(5-(methylsulfinyl)pyrimidin-2-ylamino)phenethyl)oxazolidine-3-carboxylate (454 mg, 85% purity, 95% yield) as a yellow oil. MS (ISP): 461.4 ([M+H]$^+$), 405.3 ([M+H—C$_4$H$_8$—CO$_2$]$^+$).

c) (S)-tert-Butyl 2,2-dimethyl-4-(4-(5-(methylsulfonyl)pyrimidin-2-ylamino)phenethyl)oxazolidine-3-carboxylate To a stirred solution of (4S)-tert-butyl 2,2-dimethyl-4-(4-(5-(methylsulfinyl)pyrimidin-2-ylamino)phenethyl)oxazolidine-3-carboxylate (227 mg) in dichloromethane (5 ml) was added m-CPBA (155 mg) and stirring was continued at RT for 40 min. The reaction mixture was then diluted with aq. Na$_2$SO$_3$ solution and extracted with dichloromethane. The organic layers were dried over MgSO$_4$ and concentrated in vacuo to give (S)-tert-butyl 2,2-dimethyl-4-(4-(5-(methylsulfonyl)pyrimidin-2-ylamino)phenethyl)oxazolidine-3-carboxylate (269 mg, 70% purity, 94% yield) as a brown oil. MS (ISP): 477.4 ([M+H]$^+$), 421.3 ([M+H—C$_4$H$_8$—CO$_2$]$^+$).

d) (S)-2-Amino-4-(4-(5-(methylsulfonyl)pyrimidin-2-ylamino)phenyl)butan-1-ol

The title compound was obtained in analogy to example 11 step b) using (S)-tert-butyl 2,2-dimethyl-4-(4-(5-(methylsulfonyl)pyrimidin-2-ylamino)phenethyl)oxazolidine-3-carboxylate in place of (S)-2,2-dimethyl-4-{2-[4-(5-trifluoromethyl-pyridin-2-ylamino)-phenyl]-ethyl}-oxazolidine-3-carboxylic acid tert-butyl ester. White solid. MS (ISP): 337.2 ([M+H]$^+$).

e) (S)-4-(4-(5-(Methylsulfonyl)pyrimidin-2-ylamino)phenethyl)-4,5-dihydrooxazol-2-amine The title compound was obtained in analogy to example 6 step e) using (S)-2-amino-4-(4-(5-(methylsulfonyl)pyrimidin-2-ylamino)phenyl)butan-1-ol instead of (S)-2-amino-4-[4-(4-chloro-phenylamino)-phenyl]-butan-1-ol. White solid. MS (ISP): 362.2 ([M+H]$^+$).

Example 75

(4S)-4-(4-(5-(Methylsulfinyl)pyrimidin-2-ylamino)phenethyl)-4,5-dihydrooxazol-2-amine

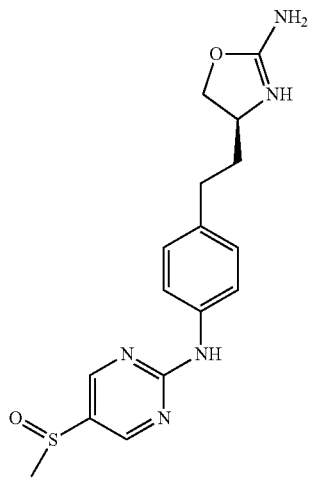 [SMILES: CS(=O)c1cnc(Nc2ccc(CC[C@H]3COC(N)=N3)cc2)nc1]

a) (2S)-2-Amino-4-(4-(5-(methylsulfinyl)pyrimidin-2-ylamino)phenyl)butan-1-ol

The title compound was obtained in analogy to example 11 step b) using (4S)-tert-butyl 2,2-dimethyl-4-(4-(5-(methylsulfinyl)pyrimidin-2-ylamino)phenethyl)oxazolidine-3-carboxylate (Example 74b) in place of (S)-2,2-dimethyl-4-{2-[4-(5-trifluoromethyl-pyridin-2-ylamino)-phenyl]-ethyl}-oxazolidine-3-carboxylic acid tert-butyl ester. Yellow oil. MS (ISP): 321.1.2 ([M+H]$^+$).

b) (4S)-4-(4-(5-(Methylsulfinyl)pyrimidin-2-ylamino)phenethyl)-4,5-dihydrooxazol-2-amine The title compound was obtained in analogy to example 6 step e) using (2S)-2-amino-4-(4-(5-(methylsulfinyl)pyrimidin-2-ylamino)phenyl)butan-1-ol instead of (S)-2-amino-4-[4-(4-chloro-phenylamino)-phenyl]-butan-1-ol. White solid. MS (ISP): 346.2 ([M+H]$^+$). The compounds of formula I and their pharmaceutically usable addition salts possess valuable pharmacological properties. Specifically, compounds of the present invention have a good affinity to the trace amine associated receptors (TAARs), especially TAAR1.

The compounds were investigated in accordance with the test given hereinafter.

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM Mg$^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described by Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Radioligand Binding Assay on Rat TAAR1
Membrane Preparation and Radioligand Binding.

HEK-293 cells stably expressing rat TAAR1 were maintained at 37° C. and 5% CO$_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without Ca$^{2+}$ and Mg$^{2+}$), pelleted at 1'000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14'000 rpm for 20 s. The homogenate was centrifuged at 48'000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14'000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (Kd) was determined via a saturation curve. The TAAR1 radioligand $^3$[H]-(S)-4-[(ethyl-phenyl-amino)-methyl]-4,5-dihydro-oxazol-2-ylamine (described in WO 2008/098857) was used at a concentration equal to the calculated Kd value, that was usually around 2.3 nM, resulting in the binding of approximately 0.2% of the radioligand and a specific binding representing approximately 85% of the total binding. Nonspecific binding was defined as the amount of $^3$[H]-(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TreffLab), and 180 µl of HEPES-NaOH (20 mM, pH 7.4) containing MgCl$_2$ (10 mM) and CaCl$_2$ (2 mM) (binding buffer), 300 µl of the radioligand $^3$[H]-(S)-4-[(ethyl-phenyl-amino)-methyl]-4,5-dihydro-oxazol-2-ylamine at a concentration of 3.3×Kd in nM and 500 µl of the membranes (resuspended at 50 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the radioactivity counted using a TopCount Microplate Scintillation Counter (Packard Instrument Company).

Radioligand Binding Assay on Mouse TAAR1
Membrane Preparation and Radioligand Binding.

HEK-293 cells stably expressing mouse TAAR1 were maintained at 37° C. and 5% CO$_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without Ca$^{2+}$ and Mg$^{2+}$), pelleted at 1'000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14'000 rpm for 20 s. The homogenate was centrifuged at 48'000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14'000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (Kd) was determined via a saturation curve. The TAAR1 radioligand $^3$[H]-(S)-4-[(ethyl-phenyl-amino)-methyl]-4,5-dihydro-oxazol-2-ylamine (described in WO 2008/098857) was used at a concentration equal to the calculated Kd value, that was usually around 0.7 nM, resulting in the binding of approximately 0.5% of the radioligand and a specific binding representing approximately 70% of the total binding. Nonspecific binding was defined as the amount of $^3$[H]-(S)-4-[(ethyl-phenyl-amino)-methyl]-4,5-dihydro-oxazol-2-ylamine bound in the presence of 10 µM unlabeled ligand. All compounds were tested at a broad range of concentrations (10 µM to 10 µM) in duplicates. The test compounds (20 µl/well) were transferred into a 96 deep well plate (TreffLab), and 180 µl of HEPES-NaOH (20 mM, pH 7.4) containing MgCl$_2$ (10 mM) and CaCl$_2$ (2 mM) (binding buffer), 300 µl of the radioligand $^3$[H]-(S)-4-[(ethyl-phenyl-amino)-methyl]-4,5-dihydro-oxazol-2-ylamine at a concentration of 3.3×Kd in nM and 500 µl of the membranes (resuspended at 60 µg protein per ml)

added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 μl of Microscint 40 (PerkinElmer) the Unifilter-96 plate was sealed and after 1 hr the radioactivity counted using a TopCount Microplate Scintillation Counter (Packard Instrument Company).

The preferred compounds show a Ki value (μM) in mouse or rat on TAAR1 in the range of <0.01 μM as shown in the table below.

| Example | Ki (μM) mouse/rat |
|---|---|
| 1 | 0.0035/0.0006 |
| 2 | 0.0021/0.0001 |
| 3 | 0.0022/0.0002 |
| 4 | 0.0021/0.0006 |
| 5 | 0.0262/0.0033 |
| 6 | 0.0002/0.0001 |
| 7 | 0.0017/0.0001 |
| 8 | 0.0002/0.0002 |
| 9 | 0.0032/0.0002 |
| 10 | 0.0001/0.0001 |
| 11 | 0.0002/0.0004 |
| 12 | 0.1111/— |
| 13 | 0.0013/0.0001 |
| 14 | 0.0008/0.0001 |
| 15 | 0.0005/0.0001 |
| 16 | 0.0015/0.0004 |
| 17 | 0.0013/0.0012 |
| 18 | 0.0012/0.0002 |
| 19 | 0.0002/0.0001 |
| 20 | 0.0224/0.004 |
| 21 | 0.02/0.0005 |
| 22 | 0.0034/0.0002 |
| 23 | 0.0003/0.0002 |
| 24 | 0.0182/0.0013 |
| 25 | 0.0035/0.0007 |
| 26 | 0.0007/0.0008 |
| 27 | 0.0182/0.004 |
| 28 | 0.001/0.0005 |
| 29 | 0.0306/0.0035 |
| 30 | 0.1339/0.0083 |
| 31 | 0.0133/0.0059 |
| 32 | 0.0019/0.0008 |
| 33 | 0.0096/0.0023 |
| 34 | 0.0387/0.0026 |
| 35 | 0.0551/0.0023 |
| 36 | 0.0047/0.0004 |
| 37 | 0.0013/0.0012 |
| 38 | 0.007/0.0007 |
| 39 | 0.0128/0.0043 |
| 40 | 0.0024/0.001 |
| 41 | 0.0593/0.0031 |
| 42 | 0.0008/0.0016 |
| 43 | 0.1072/0.0046 |
| 44 | 0.001/0.0011 |
| 45 | 0.0077/0.0013 |
| 46 | 0.0105/0.0012 |
| 47 | 0.0192/0.0024 |
| 48 | 0.0166/0.0012 |
| 49 | 0.0007/0.0006 |
| 50 | 0.0218/0.0006 |
| 51 | 0.0006/0.0004 |
| 52 | 0.0046/0.0006 |
| 53 | 0.1127/0.0265 |
| 54 | 0.0003/0.0004 |
| 55 | 0.005/0.0083 |
| 56 | 0.0019/0.0039 |
| 57 | 0.0005/0.0004 |
| 58 | 0.0002/0.0001 |
| 59 | 0.008/0.0008 |
| 60 | 0.0003/0.0002 |
| 61 | 0.0007/0.0002 |
| 62 | 0.0623/0.0132 |
| 63 | 0.0084/0.0022 |
| 64 | 0.063/0.002 |
| 65 | 0.0244/0.0032 |
| 66 | 0.023/0.0064 |
| 67 | 0.0412/0.0084 |
| 68 | 0.0651/0.0265 |
| 69 | 0.0355/0.0407 |
| 70 | 0.1341/0.0205 |
| 71 | 0.0137/0.0011 |
| 72 | 0.0019/0.0007 |
| 73 | 0.02/0.0028 |
| 74 | 0.046/0.0146 |
| 75 | 0.4802/0.1044 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety and attention deficit hyperactivity disorder (ADHD).

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| Item | Ingredients | mg/tablet | | | |
|---|---|---|---|---|---|
| | | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredients | mg/capsule | | | |
|---|---|---|---|---|---|
| | | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:
1. A compound of formula I

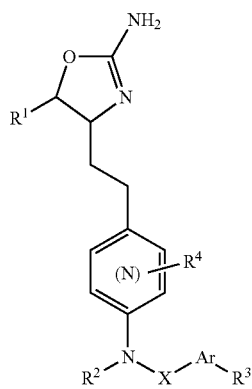

wherein
$R^1$ is hydrogen or lower alkyl;
$R^2$ is hydrogen;
$R^3$ is hydrogen, halogen, lower alkyl, lower alkyl substituted by halogen, lower alkoxy, lower alkoxy substituted by halogen, cyano, S-lower alkyl, S(O)-lower alkyl, $S(O)_2$-lower alkyl, C(O)-lower alkyl or $C_{3-6}$-cycloalkyl;
$R^4$ is hydrogen or lower alkyl;

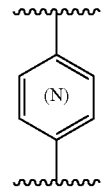

is phenyl;
X is a bond or —$CH(CF_3)$—; and
Ar is aryl, optionally substituted by one or more $R^3$;
or a pharmaceutically acceptable acid addition salt thereof.
2. The compound of claim 1, having formula Ia

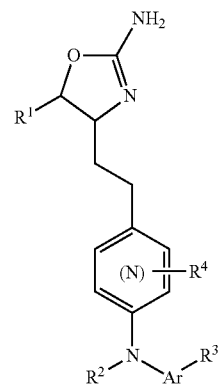

wherein
$R^1$ is hydrogen or lower alkyl;
$R^2$ is hydrogen;
$R^3$ is hydrogen, halogen, lower alkyl, lower alkyl substituted by halogen, lower alkoxy, lower alkoxy substituted by halogen, cyano, S-lower alkyl, S(O)-lower alkyl, $S(O)_2$-lower alkyl, C(O)-lower alkyl or $C_{3-6}$-cycloalkyl;
$R^4$ is hydrogen or lower alkyl;

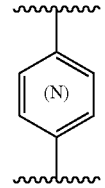

is phenyl; and
Ar is aryl, optionally substituted by one or more $R^3$;
or a pharmaceutically acceptable acid addition salt thereof.
3. The compound of claim 2, wherein Ar is phenyl or naphthtyl.
4. The compound of claim 3, selected from the group consisting of (S)-4-(4-(Naphthalen-1-ylamino)phenethyl)-4,5-dihydrooxazol-2-amine;
(S)-4-(4-(8-Chloronaphthalen-1-ylamino)phenethyl)-4,5-dihydrooxazol-2-amine;
(S)-4-{2-[4-(4-Chloro-phenylamino)-phenyl]-ethyl}-4,5-dihydro-oxazol-2-ylamine;
(S)-4-{2-[4-(4-Chloro-2-fluoro-phenylamino)-phenyl]-ethyl}-4,5-dihydro-oxazol-2-ylamine;
(S)-4-{2-[4-(4-Trifluoromethyl-phenylamino)-phenyl]-ethyl}-4,5-dihydro-oxazol-2-ylamine;
(S)-4-{2-[4-(4-Methoxy-phenylamino)-phenyl]-ethyl}-4,5-dihydro-oxazol-2-ylamine;
(S)-4-(4-(3-Methyl-4-(trifluoromethoxy)phenylamino)phenethyl)-4,5-dihydrooxazol-2-amine;
(S)-4-[2-(4-Phenylamino-phenyl)-ethyl]-4,5-dihydro-oxazol-2-ylamine;
(S)-4-(4-(p-Tolylamino)phenethyl)-4,5-dihydrooxazol-2-amine and
(S)-4-(4-(3,4-Dichlorophenylamino)phenethyl)-4,5-dihydrooxazol-2-amine.

5. The compound of claim 1, having formula Ib

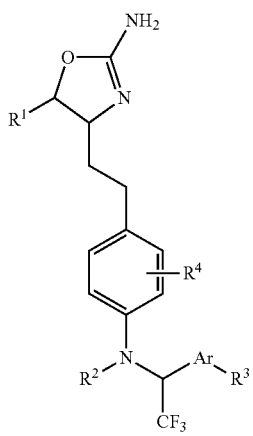

Ib wherein
$R^1$ is hydrogen or lower alkyl;
$R^2$ is hydrogen;
$R^3$ is hydrogen, halogen, lower alkyl, lower alkyl substituted by halogen, lower alkoxy, lower alkoxy substituted by halogen, cyano, S-lower alkyl, S(O)-lower alkyl, $S(O)_2$-lower alkyl, C(O)-lower alkyl or $C_{3-6}$-cycloalkyl;
$R^4$ is hydrogen or lower alkyl;

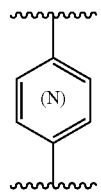

is phenyl;
Ar is aryl, optionally substituted by one or more $R^3$;
or a pharmaceutically acceptable acid addition salt thereof.

6. The compound of claim 5, wherein Ar is phenyl or naphthtyl.

7. The compound of claim 5, selected from the group consisting of:
(4S)-4-(4-(1-(4-Chlorophenyl)-2,2,2-trifluoroethylamino)phenethyl)-4,5-dihydrooxazol-2-amine (1:1 mixture of epimers);
(+)-(S)-4-(4-((S)-1-(4-Chlorophenyl)-2,2,2-trifluoroethylamino)phenethyl)-4,5-dihydrooxazol-2-amine;
(−)-(S)-4-(4-((R)-1-(4-chlorophenyl)-2,2,2-trifluoroethylamino)phenethyl)-4,5-dihydrooxazol-2-amine;
(4S)-4-(4-(2,2,2-Trifluoro-1-(3-fluorophenyl)ethylamino) phenethyl)-4,5-dihydrooxazol-2-amine and
(4S)-4-(4-(2,2,2-Trifluoro-1-(4-(trifluoromethyl)phenyl) ethylamino)phenethyl)-4,5-dihydrooxazol-2-amine.

8. A pharmaceutical composition comprising a compound of formula I

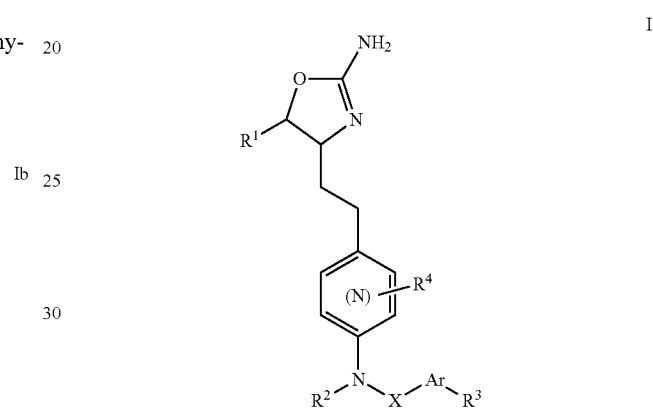

I wherein
$R^1$ is hydrogen or lower alkyl;
$R^2$ is hydrogen;
$R^3$ is hydrogen, halogen, lower alkyl, lower alkyl substituted by halogen, lower alkoxy, lower alkoxy substituted by halogen, cyano, S-lower alkyl, S(O)-lower alkyl, $S(O)_2$-lower alkyl, C(O)-lower alkyl or $C_{3-6}$-cycloalkyl;
$R^4$ is hydrogen or lower alkyl;

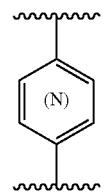

is phenyl;
X is a bond or —$CH(CF_3)$—; and
Ar is aryl, optionally substituted by one or more $R^3$;
or a pharmaceutically acceptable acid addition salt thereof and a pharmaceutically acceptable carrier.

9. The composition of claim 8, wherein the compound of formula I is a compound of formula Ia.

10. The composition of claim 8, wherein the compound of formula I is a compound of formula Ib.

* * * * *